(12) United States Patent
Freeman et al.

(10) Patent No.: US 10,716,949 B2
(45) Date of Patent: Jul. 21, 2020

(54) CHANGING CARDIAC SHOCK DELIVERY PARAMETERS BASED ON A TRANSFORM VALUE

(71) Applicant: ZOLL Medical Corporation, Chelmsford, MA (US)

(72) Inventors: Gary A. Freeman, Waltham, MA (US); Weilun Quan, Dracut, MA (US); Christopher Luke Kaufman, Somerville, MA (US); Kent Volosin, Mars, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 170 days.

(21) Appl. No.: 15/924,969

(22) Filed: Mar. 19, 2018

(65) Prior Publication Data
US 2019/0282823 A1    Sep. 19, 2019

(51) Int. Cl.
*A61N 1/39* (2006.01)
*A61N 1/04* (2006.01)
*A61B 5/0408* (2006.01)

(52) U.S. Cl.
CPC ......... *A61N 1/3993* (2013.01); *A61N 1/0484* (2013.01); *A61N 1/0496* (2013.01);
(Continued)

(58) Field of Classification Search
CPC .. A61N 1/3993; A61N 1/0496; A61N 1/0484; A61N 1/3943; A61N 1/3904;
(Continued)

(56) References Cited

U.S. PATENT DOCUMENTS 5,046,504 A    9/1991  Albert
5,077,667 A   12/1991  Brown et al.
(Continued)

FOREIGN PATENT DOCUMENTS

JP    2005-339533    12/2005
JP    2015-527097     9/2015
(Continued)

OTHER PUBLICATIONS

Chaudhry, Fahd A., A Novel Resuscitation Algorithm Using Waveform Analysis and End-Tidal Carbon Dioxide Pressure for Ventricular Fibrillation, University of Arizona, Biomedical Engineering Interdisciplinary Program, 2011, 39 pages.
(Continued)

*Primary Examiner* — Catherine M Voorhees
(74) *Attorney, Agent, or Firm* — Fish & Richardson P.C.

(57) ABSTRACT

A medical device that includes a power source, a therapy delivery interface, therapy electrodes, electrocardiogram (ECG) sensing electrodes to sense ECG signal of a heart of a patient, a sensor interface to receive and digitize the ECG signal, and a processor. The processor is configured to analyze the ECG signal to determine a cardiac rhythm and a transform value representing a magnitude of a frequency component of the cardiac rhythm, analyze the cardiac rhythm and the transform value to detect a shockable cardiac arrhythmia by classifying the cardiac rhythm as a noise rhythm or a shockable cardiac arrhythmia rhythm based on the transform value, and causing the processor to detect the cardiac arrhythmia if classifying the cardiac rhythm as a shockable cardiac arrhythmia rhythm, initiate a treatment alarm sequence, adjust the shock delivery parameter for a defibrillation shock, and provide the defibrillation shock via the therapy electrodes.

37 Claims, 13 Drawing Sheets

(52) U.S. Cl.
CPC ......... *A61N 1/3904* (2017.08); *A61N 1/3943* (2013.01); *A61N 1/3987* (2013.01); *A61B 5/0408* (2013.01); *A61N 1/046* (2013.01); *A61N 1/39044* (2017.08)

(58) Field of Classification Search
CPC .. A61N 1/39044; A61N 1/046; A61N 1/3987; A61N 1/0476; A61N 1/3621; A61N 1/08; A61N 1/3981; A61N 1/3968; A61N 1/3937; A61N 1/3625; A61B 5/0408
See application file for complete search history.

(56) References Cited

U.S. PATENT DOCUMENTS

| | | | |
|---|---|---|---|
| 5,092,341 | A | 3/1992 | Kelen |
| 5,741,304 | A | 4/1998 | Patwardhan et al. |
| 5,944,669 | A | 8/1999 | Kaib |
| 5,957,856 | A | 9/1999 | Weil et al. |
| 6,148,233 | A * | 11/2000 | Owen .................. A61N 1/0452 607/5 |
| 6,171,257 | B1 | 1/2001 | Weil |
| 6,224,562 | B1 | 5/2001 | Lurie et al. |
| 6,760,621 | B2 | 7/2004 | Walcott |
| 6,813,517 | B2 | 11/2004 | Daynes et al. |
| 7,269,454 | B2 | 9/2007 | Sherman |
| 7,593,772 | B2 | 9/2009 | Sherman |
| 7,774,060 | B2 | 8/2010 | Westenkow |
| 7,813,791 | B1 | 10/2010 | Gill |
| 7,831,299 | B2 | 11/2010 | Tan et al. |
| 7,920,917 | B2 | 4/2011 | Kelly |
| 8,165,671 | B2 | 4/2012 | Freeman et al. |
| 8,868,179 | B2 | 10/2014 | Quan et al. |
| 8,948,859 | B2 | 2/2015 | Freeman et al. |
| 8,989,837 | B2 | 3/2015 | Weinstein et al. |
| 9,180,304 | B2 | 11/2015 | Quan et al. |
| 9,186,521 | B2 | 11/2015 | Quan et al. |
| 9,480,853 | B2 | 11/2016 | Quan et al. |
| 9,579,515 | B2 | 2/2017 | Quan et al. |
| 9,592,402 | B2 | 3/2017 | Quan et al. |
| 9,782,093 | B2 | 10/2017 | Quan et al. |
| 9,907,477 | B2 | 3/2018 | Quan et al. |
| 2002/0026229 | A1 | 2/2002 | Weil et al. |
| 2002/0133197 | A1 | 9/2002 | Snyder et al. |
| 2002/0138106 | A1 | 9/2002 | Chiristini et al. |
| 2003/0055460 | A1 | 3/2003 | Owen et al. |
| 2004/0039419 | A1 | 2/2004 | Stickney et al. |
| 2004/0116969 | A1 | 6/2004 | Owen |
| 2004/0215271 | A1 | 10/2004 | Sullivan |
| 2005/0080828 | A1 | 5/2005 | Johnson |
| 2005/0245974 | A1 | 11/2005 | Sherman |
| 2005/0267536 | A1 | 12/2005 | Freeman et al. |
| 2006/0025824 | A1 | 2/2006 | Freeman |
| 2006/0116724 | A1 | 6/2006 | Synder |
| 2007/0060785 | A1 | 3/2007 | Freeman et al. |
| 2007/0100381 | A1 | 5/2007 | Snyder et al. |
| 2008/0145827 | A1 | 6/2008 | Strand et al. |
| 2008/0208070 | A1 | 8/2008 | Snyder et al. |
| 2009/0270930 | A1 | 10/2009 | Walker |
| 2009/0281413 | A1 | 11/2009 | Boyden |
| 2010/0268059 | A1 | 10/2010 | Ryu et al. |
| 2010/0298899 | A1 * | 11/2010 | Donnelly ........... A61B 5/02055 607/6 |
| 2011/0021938 | A1 | 1/2011 | Anderson et al. |
| 2011/0034816 | A1 | 2/2011 | Tan et al. |
| 2011/0202100 | A1 | 8/2011 | Tan et al. |
| 2011/0202101 | A1 | 8/2011 | Tan et al. |
| 2011/0295127 | A1 | 12/2011 | Sandler et al. |
| 2012/0010543 | A1 | 1/2012 | Johnson et al. |
| 2012/0046706 | A1 | 2/2012 | Anderson et al. |
| 2012/0191024 | A1 | 4/2012 | Halperin et al. |
| 2012/0226178 | A1 | 9/2012 | Freeman et al. |
| 2013/0138168 | A1 | 5/2013 | Quan et al. |
| 2013/0144181 | A1 | 6/2013 | Fogt et al. |
| 2013/0190634 | A1 | 7/2013 | Phillips |
| 2013/0218057 | A1 * | 8/2013 | Jorgenson ........... A61N 1/3987 601/41 |
| 2013/0331719 | A1 * | 12/2013 | Freeman ................ A61B 5/046 600/518 |
| 2014/0005738 | A1 | 1/2014 | Jorgenson et al. |
| 2014/0107541 | A1 | 4/2014 | Sullivan |
| 2014/0236030 | A1 | 8/2014 | Tan et al. |
| 2014/0277224 | A1 | 9/2014 | Quan et al. |
| 2014/0277228 | A1 | 9/2014 | Quan et al. |
| 2015/0065815 | A1 | 3/2015 | Najarian |
| 2015/0126885 | A1 | 5/2015 | Freeman et al. |
| 2015/0257709 | A1 | 9/2015 | Quan et al. |
| 2015/0257715 | A1 | 9/2015 | Quan et al. |
| 2015/0352367 | A1 | 12/2015 | Quan et al. |
| 2015/0352369 | A1 | 12/2015 | Quan et al. |
| 2016/0023010 | A1 | 1/2016 | Quan et al. |
| 2016/0082278 | A1 | 3/2016 | Quan et al. |
| 2017/0209706 | A1 | 7/2017 | Quan et al. |
| 2017/0361120 | A1 * | 12/2017 | Liu ......................... A61B 5/72 |
| 2018/0055442 | A1 | 3/2018 | Freeman |
| 2018/0220913 | A1 | 8/2018 | Quan et al. |
| 2018/0304088 | A1 | 10/2018 | Quan et al. |
| 2019/0054307 | A1 | 2/2019 | Quan et al. |
| 2019/0261878 | A1 | 8/2019 | Quan |
| 2019/0365264 | A1 | 12/2019 | Freeman |

FOREIGN PATENT DOCUMENTS

| | | |
|---|---|---|
| WO | WO 2011/100534 | 8/2011 |
| WO | WO 2012/059846 | 5/2012 |
| WO | WO 2012/072518 | 6/2012 |
| WO | WO 2013/071280 | 5/2013 |

OTHER PUBLICATIONS

Chinese Office Action, CN Application 201480027256.X, dated May 30, 2016, 8 pages.

Compos et al., "An Up-Down Bayesian, Defibrillation Efficacy Estimator", Pace-Pacing and Clinical Electrophysiology, Blackwell Futura Publishing, Malden, MA, US, vol. 20, No. 5, Part 01, May 1, 1997, pp. 1292-1300.

European Search Report, 14768658.8, dated Feb. 12, 2016, 10 pages.

Extended European Search Report, European Patent Application No. 13804051.4, dated Feb. 4, 2016, 9 pages.

Extended European Search Report, PCT/US2012/064779, dated Aug. 14, 2015, 7 pages.

Huang et al, "Quantification of activation patterns during ventricular fibrillation in open-chest porcine left ventricle and septum", Heart Rhythm Elsevier, US, vol. 2, No. 7, Jul. 1, 2005, pp. 720-728.

International Preliminary Report on Patentability issued in international application No. PCT/US2016/023992, dated Sep. 26, 2017, 9 pages.

International Search Report and Written Opinion from corresponding PCT/US2013/44750 dated Sep. 20, 2013.

International Search Report and Written Opinion dated Jun. 10, 2016 in international application No. PCT/US2016/023992, 7 pgs.

International Search Report and Written Opinion, PCT/US2012/64779, dated Feb. 1, 2013, 7 pages.

International Search Report and Written Opinion, PCT/US2014/027431, dated Aug. 11, 2014, 9 pages.

International Search Report and Written Opinion, PCT/US2014/27514, dated Aug. 11, 2014, 8 pages.

International Search Report and Written Opinion, PCT/US2014/27658, dated Aug. 25, 2014, 13 pages.

International Search Report and Written Opinion, PCT/US2015/35174, dated Sep. 17, 2015, 8 pages.

International Search Report and Written Opinion, PCT/US2015/35189, dated Nov. 3, 2015, 15 pages.

Lee, Seungyup, "Mapping the Characteristics of Atrial Activation Patterns During Atrial Fibrillation," Case Western Reserve University: Department of Biomedical Engineering, Jan. 2013, 34 pages.

Povoas et al., "Predicting the success of defibrillation by electrocardiographic analysis," Resuscitation 53(1):77-82 (2002).

(56) References Cited

OTHER PUBLICATIONS

Supplementary European Search Report, dated Nov. 4, 2016 for EP Application No. 14768107.6, 3 pages.
U.S. Office Action in U.S. Appl. No. 15/868,277, dated Jun. 4, 2018, 6 pages.
Wang et al., "Fourier Analysis in Polar and Spherical Coordinates," Internal Report Jan. 2008, Albert-Ludwigs University Freiburg, 2008, 26 pages.
Wang, et al., "Rotational Invariance Based on Fourier Analysis in Polar and Spherical Coordinates," IEEE Transactions on Pattern Analysis and Machine Intelligence, vol. 31, No. 9, Sep. 2009.
Watson et al., "Rapid Communication; Wavelet transform-based prediction of the likelihood of successful defibrillation for patients exhibiting ventricular fibrillation; Rapid Communication", Measurement Science and Technology, IOP, Bristol, GB, vol. 16, No. 10, Oct. 1, 2005, pp. L1-L6.
U.S. Office Action in U.S. Appl. No. 15/658,908, dated Jul. 2, 2018, 8 pages.

\* cited by examiner

CHANGING CARDIAC SHOCK DELIVERY PARAMETERS BASED ON A TRANSFORM VALUE

TECHNICAL FIELD

The technology described in this document is directed to non-invasive medical devices, and more particularly, to a non-invasive ambulatory medical monitoring and treatment device that is capable of externally defibrillating and/or externally pacing the heart of a patient wearing the device.

BACKGROUND

Cardiac arrest and other cardiac health ailments are a major cause of death worldwide. Various resuscitation efforts aim to maintain the body's circulatory and respiratory systems during cardiac arrest in an attempt to save the life of the victim. Such resuscitation efforts may include CPR (i.e., chest compressions with or without artificial respiration), pacing, defibrillation, drug therapy, open heart massage, or various combinations thereof. For many forms of cardiac arrest, such as where the subject is suffering from Ventricular Fibrillation (VF) or Ventricular Tachycardia (VT), defibrillation may be appropriate, especially if applied soon after the onset of VF or VT. Various studies have shown that each minute of delay in the application of defibrillation can result in a 10% decrease in the victim's chance of survival, thus the sooner the resuscitation efforts begin, the better the victim's chances of survival.

SUMMARY

In accordance with one aspect of the present invention, an ambulatory medical monitoring and treatment device includes: a power source, a therapy delivery interface, coupled to the power source, a plurality of therapy electrodes coupled to the therapy delivery interface, a plurality of electrocardiogram (ECG) sensing electrodes to sense ECG signal of a heart of a patient, a sensor interface to receive and digitize the ECG signal, and at least one processor coupled to the sensor interface and the therapy delivery interface, the at least one processor configured to: analyze the ECG signal to determine a cardiac rhythm and a transform value that represents a magnitude of at least one frequency component of the cardiac rhythm, analyze the cardiac rhythm and the transform value to detect a shockable cardiac arrhythmia by classifying the cardiac rhythm as one of a noise rhythm and a shockable cardiac arrhythmia rhythm based at least in part on the transform value, and causing the at least one processor to detect the cardiac arrhythmia in response to classifying the cardiac rhythm as a shockable cardiac arrhythmia rhythm, initiate a treatment alarm sequence requesting a response from the patient to verify that the patient is unconscious in response to detecting the shockable cardiac arrhythmia, adjust, based on the transform value, at least one shock delivery parameter for a defibrillation shock, and cause the therapy delivery interface to provide the defibrillation shock via the plurality of therapy electrodes based on the at least one shock delivery parameter on receiving no response from the patient.

In some implementations, the at least one processor is configured to initiate the treatment alarm sequence to generate an alert in response to detecting the shockable cardiac arrhythmia, the alert indicating detection of the shockable cardiac arrhythmia. In some implementations, the at least one processor is configured to initiate a release of a conductive gel on the patient's chest. In some implementations, the alert is a first alert and prior to initiating the release of the conductive gel, the at least one processor is configured to generate a second alert indicating shock delivery. In some implementations, the transform value is a first transform value and the at least one processor is configured to determine a second transform value after release of the conductive gel and prior to providing the defibrillation shock. In some implementations, the at least one processor is configured to perform a comparison between the first transform value and the second transform value and adjust the at least one shock delivery parameter based on the comparison. In some implementations, the first transform value and the second transform value are determined over a window of time of 100 milliseconds to twenty seconds. In some implementations, the first alert is generated over a window of time of about twenty seconds and the second alert is generated over a window of time of about fifteen seconds. In some implementations, the at least one shock delivery parameter is a peak current value. In some implementations, the at least one shock delivery parameter is defibrillation energy waveform duration. In some implementations, the at least one shock delivery parameter is at least one of a defibrillation current waveform rise time, a shock energy, and a defibrillation peak voltage. In some implementations, generating the transform value includes applying one or more Fast Fourier Transforms (FFTs) to data representing the ECG signal. In some implementations, the FFTs include vectorized FFTs applied to vectors formed from data obtained by different leads for the ECG signal. In some implementations, generating the transform value includes one or more amplitude spectrum area calculations applied to the data representing the ECG signal. In some implementations, generating the transform value includes computing a mathematical transform from a time domain to a frequency domain on a window of the ECG signal. In some implementations, generating the transform value includes summing products of a plurality of magnitudes of frequency components with a plurality of weighting factors within a predetermined spectrum. In some implementations, the plurality of weighting factors is in a nonlinear relationship with the frequency components within the predetermined spectrum. In some implementations, the plurality of weighting factors has a pre-established linear or nonlinear relationship with the magnitudes of the frequency components. In some implementations, the sensor interface receives an additional parameter indicative of a state of the patient, the additional parameter includes a cardiac information or a non-cardiac information. In some implementations, the at least one processor is configured to adjust the at least one shock delivery parameter for the defibrillation shock based on the additional parameter.

In accordance with another aspect of the present invention, an ambulatory medical monitoring and treatment device includes: a power source, a therapy delivery interface, coupled to the power source, a plurality of therapy electrodes coupled to the therapy delivery interface, a plurality of electrocardiogram (ECG) sensing electrodes to sense ECG signal of a heart of a patient, a sensor interface to receive and digitize the ECG signal, and at least one processor coupled to the sensor interface and the therapy delivery interface, the at least one processor configured to: analyze the ECG signal to detect a shockable cardiac arrhythmia, determine, from the ECG signal, a first transform value that represents a magnitude of at least one frequency component of the ECG signal, confirm, based at least in part on the first transform value, that the ECG signal includes the shockable cardiac arrhythmia rhythm, initiate a treatment alarm sequence requesting a response from the patient to verify that the patient is unconscious, determine, from the ECG signal, a second transform value that represents another magnitude of another at least one frequency component of the shockable cardiac arrhythmia rhythm, adjust, based on the first transform value and the second transform value, at least one shock delivery parameter for a defibrillation shock, and cause the therapy delivery interface to provide the defibrillation shock via the plurality of therapy electrodes based on the at least one shock delivery parameter receiving no response from the patient.

In accordance with another aspect of the present invention, a computer-implemented method for providing ambulatory medical monitoring and treatment to a patient, the method being executed using one or more processors and includes: receiving, by the one or more processors, an electrocardiogram (ECG) signal of a heart of a patient, analyzing, by the one or more processors, the ECG signal to determine a cardiac rhythm and a transform value that represents a magnitude of at least one frequency component of the cardiac rhythm, analyzing, by the one or more processors, the cardiac rhythm and the transform value to detect a shockable cardiac arrhythmia by classifying the cardiac rhythm as one of a noise rhythm and a shockable cardiac arrhythmia rhythm based at least in part on the transform value, and causing the at least one processor to detect the cardiac arrhythmia in response to classifying the cardiac rhythm as a shockable cardiac arrhythmia rhythm, initiating, by the one or more processors, a treatment alarm sequence requesting a response from the patient to verify that the patient is unconscious in response to detecting the shockable cardiac arrhythmia, adjusting, by the one or more processors, based on the transform value, at least one shock delivery parameter for a defibrillation shock, and causing, by the one or more processors, a therapy delivery interface to provide the defibrillation shock via a plurality of therapy electrodes based on the at least one shock delivery parameter on receiving no response from the patient.

DETAILED DESCRIPTION

Figure 1A:
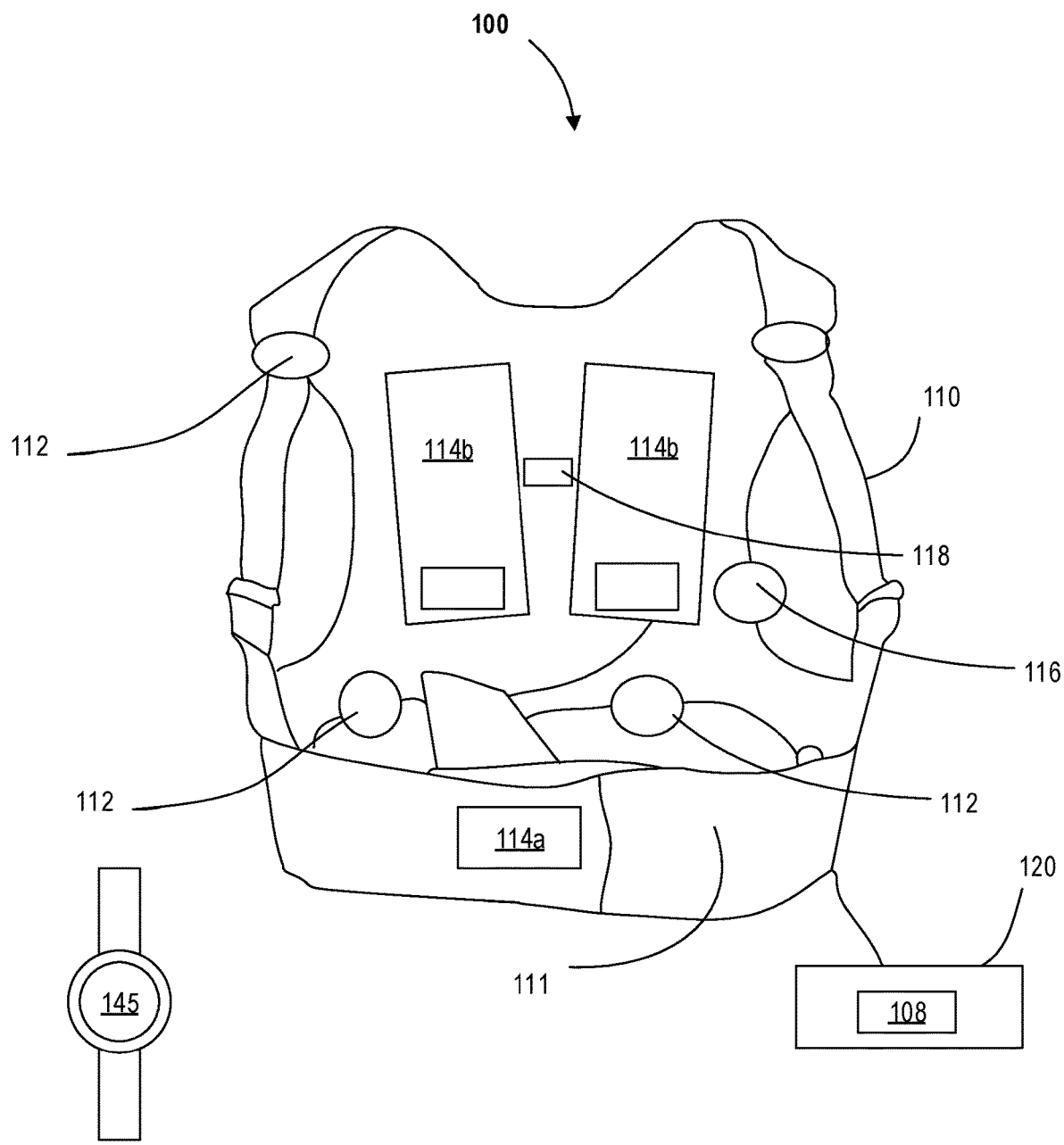
FIGS. 1A and 1B illustrate a medical monitoring and treatment device, such as a wearable defibrillator.

This disclosure relates to the use of one or more transform values based on frequency components of electrocardiogram (ECG) signals received from a cardiac monitoring and treatment device worn by a patient in adjusting treatment delivered to the patient. For example, the one or more transform values can be used to determine appropriate energy pulse characteristics for converting a ventricular tachycardia (VT) or ventricular fibrillation (VT) event. The one or more transform values can include or be based on area of an amplitude spectrum (AMSA) transform value as described in further detail below.

In certain implementations, the transform value score can also be used to classify an ECG rhythms as a noise rhythm, a sinus rhythm, or shockable cardiac arrhythmia rhythms, such as a shockable VT or shockable VF rhythms. As the transform value includes information on the frequency content of the ECG signal, the transform value can be used to classify shockable cardiac arrhythmia rhythms in devices that operate in high-noise environments, such as a wearable cardioverter defibrillator. In examples given below, an ambulatory monitoring and treatment device can use the transform value to confirm a shockable cardiac arrhythmia determination and further to adjust one or more treatment parameters.

In certain implementations, the ambulatory device can calculate first and second transform values at different times, e.g., once early in an arrhythmia alert and/or treatment sequence and a second time later during the sequence prior to providing a shock to the patient. For example, a first transform value can be calculated at the onset of a shockable VT/VF classification. Based on the first transform value, one or more energy pulse characteristics are adjusted in preparation for the shock delivery. The patient is alerted in an escalating manner (e.g., first a vibration alert, then multiple siren and audible alerts along with visual indicators). If the patient does not respond to suspend the treatment alarm sequence, the ambulatory device continues with the sequence by causing gel to deploy on the therapy electrodes. A second transform value can be calculated during or after gel deploy and immediately prior to delivering the energy pulse to the body of the patient. The energy pulse characteristics can be further refined based on the second transform value. Additional details on these embodiments are provided below.

The examples of the methods and apparatus discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples.

Any references to examples or elements or acts of the systems and methods herein referred to in the singular may also embrace examples including a plurality of the elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Aspects and embodiments of the present technology monitor the cardiac condition of a patient and administer external therapy to the heart using a non-invasive medical monitoring and treatment device, and in some embodiments monitor the cardiac condition of a patient and administer external therapy to the heart using a bodily-attached non-invasive ambulatory medical monitoring and treatment device. In some embodiments, the technology described herein may also be used in invasive devices. As used herein, the term non-invasive means that the device does not penetrate the body of a patient. In contrast, invasive devices, such as implantable medical devices, at least a portion of the device is disposed subcutaneously. The term bodily-attached means that at least a portion of the device (other than its electrodes in the case of a defibrillator, cardioverter or pacer) is removably attached to the body of a patient, such as by mechanical coupling (for example, by a wrist strap, cervical collar, bicep ring), adhesion (for example, by an adhesive gel intermediary), suction, magnetism, fabric or other flexible material (for example, by straps or integration into a garment) or other body mounting features not limited by the aforementioned examples. The coupling elements hold the device in a substantially fixed position with respect to the body of the patient. The term ambulatory means that the device is capable of, and designed for, moving with the patient as the patient goes about their daily routine.

Although embodiments of the present technology are primarily directed to non-invasive bodily-attached ambulatory medical monitoring and treatment devices, various aspects of the present technology may be adapted for use in other types of non-invasive medical monitoring and treatment devices that are not adapted to be worn by a patient, such as an Automated External Defibrillator (AED) or an Advanced Life Support (ALS) type of defibrillator, such as the M Series defibrillator, R Series ALS defibrillator, R Series Plus defibrillator, or E Series defibrillator manufactured by the ZOLL Medical Corporation of Chelmsford Mass.

One example of a non-invasive bodily-attached ambulatory medical monitoring and treatment device is the LifeVest® Wearable Cardioverter Defibrillator available from ZOLL Medical Corporation of Chelmsford, Mass. The medical monitoring and treatment device can provide lifesaving defibrillation treatment to a patient suffering from a treatable form of cardiac arrhythmia such as Ventricular Fibrillation (VF) or Ventricular Tachycardia (VT). The medical monitoring and treatment device can be configured for continuous use by the patient. In some implementations, the continuous use can be substantially or nearly continuous in nature. That is, the medical monitoring and treatment device may be continuously used, except for sporadic periods, during which the use temporarily ceases (e.g., while the patient bathes, while the patient is refit with a new and/or a different garment, while the battery is charged/changed, while the garment is laundered, etc.). Such substantially or nearly continuous use as described herein may nonetheless qualify as continuous use. In some implementations, the patient may remove the medical monitoring and treatment device for a short portion of the day (e.g., for half an hour to bathe).

Further, the medical monitoring and treatment device can be configured as a long term or extended use medical device. Such devices can be configured for use by the patient for an extended period of 24 hours or more, several days, weeks, months, or even years. Accordingly, the extended use can be uninterrupted until a physician or other caregiver provides specific prescription to the patient to stop use of the medical monitoring and treatment device. For example, the medical monitoring and treatment device can be prescribed for use by a patient for an extended period of at least one week. In an example, the medical monitoring and treatment device can be prescribed for use by a patient for an extended period of at least 30 days. In an example, the medical monitoring and treatment device can be prescribed for use by a patient for an extended period of at least one month. In an example, the medical monitoring and treatment device can be prescribed for use by a patient for an extended period of at least two months. In an example, the medical monitoring and treatment device can be prescribed for use by a patient for an extended period of at least three months. In an example, the medical monitoring and treatment device can be prescribed for use by a patient for an extended period of at least six months. In an example, the medical monitoring and treatment device can be prescribed for use by a patient for an extended period of at least one year.

Regardless of the extended period of wear, the use of the medical monitoring and treatment device can include continuous or nearly continuous wear by the patient as described above. For example, the continuous use can include continuous wear or attachment of the medical monitoring and treatment device to the patient. In implementations, the continuous attachment is through one or more of the electrodes as described herein during both periods of monitoring and periods when the device may not be monitoring the patient but is otherwise still worn by or otherwise attached to the patient. Continuous use can include continuously monitoring the patient while the patient is wearing the device for cardiac-related information (e.g., electrocardiogram (ECG) information, including arrhythmia information, heart vibrations, etc.), and/or non-cardiac information (e.g., blood oxygen, the patient's temperature, glucose levels, tissue fluid levels, and/or lung vibrations). The medical monitoring and treatment device can perform monitoring and/or recording operations in periodic or aperiodic time intervals or times (e.g., every few minutes, hours, once a day, once a week, or other interval set by a technician or prescribed by a caregiver). For example, the monitoring and/or recording can be triggered by a user action or another event.

Figure 1B:
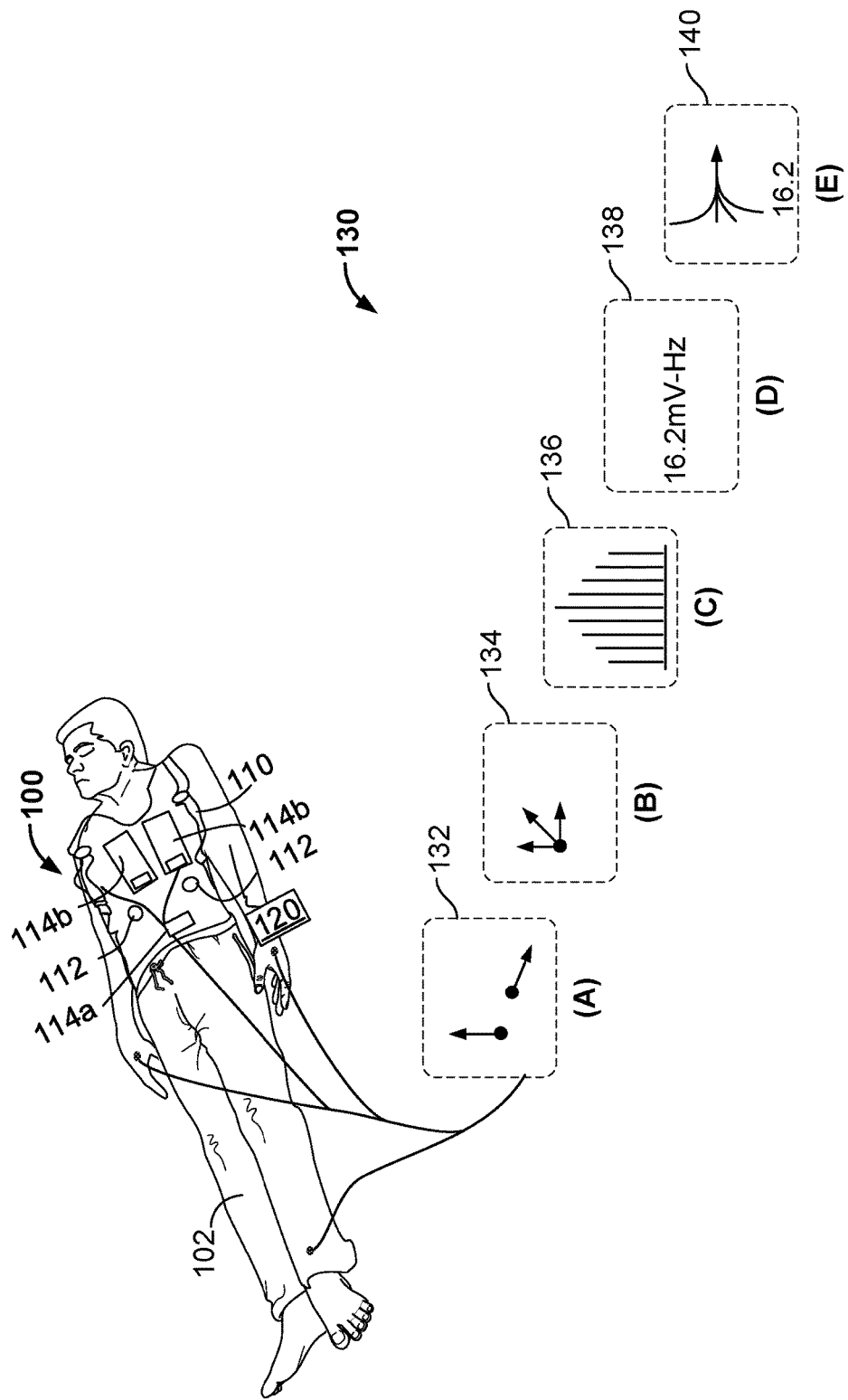

FIGS. 1A and 1B illustrate a medical monitoring and treatment device, such as a LifeVest® Wearable Cardioverter Defibrillator available from ZOLL Medical Corporation of Chelmsford, Mass. As shown in FIG. 1A, the medical monitoring and treatment device 100 includes a harness 110 having a pair of shoulder straps and a belt 111 that is worn about the torso of a patient. The harness 110 is typically made from a material, such as cotton, nylon, spandex, or combinations thereof that is breathable, and unlikely to cause skin irritation, even when worn for prolonged periods of time. The medical monitoring and treatment device 100 includes a plurality of electrocardiographic (ECG) sensing electrodes 112 that are disposed on or in the harness 110 at various positions about the patient's body and electrically coupled (wirelessly or by a wired connection) to a portable treatment controller 120 via a connection pod. The plurality of ECG sensing electrodes 112 are used by the portable treatment controller 120 to monitor the cardiac function of the patient and generally include a front/back pair of ECG sensing electrodes and a side/side pair of ECG sensing electrodes. In some embodiments, additional ECG sensing electrodes may be provided, and the plurality of ECG sensing electrodes 112 may be disposed at varying locations about the patient's body. In addition, the plurality of ECG electrodes 112 may incorporate any electrode system, including conventional stick-on adhesive electrodes, conductive electrodes with gel deployment, e.g., metallic electrodes with stored conductive gel configured to be dispersed in the electrode-skin interface when needed, dry-sensing ECG electrodes, e.g., a metallic substrate with an oxide layer in direct contact with the patient's skin, radio transparent electrodes, segmented electrodes, or one or more long-term wear electrodes that are configured to be continuously worn by a patient for extended periods (e.g., 3 or more days). Signals from various combinations of pairs of the plurality of ECG electrodes can be used to define different channels of the ECG signal. For example, signals measured using a particular pair of electrodes can be used to obtain a differential signal to define a corresponding channel of the ECG signal. The medical monitoring and treatment devices disclosed herein may incorporate sundry materials arranged in a variety of configurations to maintain a proper fit with the patient's body. Thus embodiments are not limited to the configuration and materials described above with reference to FIG. 1.

The medical monitoring and treatment device 100 can include a plurality of therapy electrodes 114 that are electrically coupled to the portable treatment controller 120 via the connection pod and which are configured to deliver one or more therapeutic defibrillating shocks to the body of the patient, if it is determined that such treatment is warranted. In some embodiments, the plurality of therapy electrodes may also be configured to perform cardiac pacing, or to apply an electrical shock that can terminate a cardiac arrhythmia, such as VT. As shown, the plurality of therapy electrodes 114 includes a first therapy electrode 114a that is disposed on the front of the patient's torso and a second therapy electrode 114b that is disposed on the back of the patient's torso. The second therapy electrode 114b may, as shown, include a pair of therapy electrodes that are electrically coupled together and act as the second therapy electrode 114b. The use of two therapy electrodes 114a, 114b permits a biphasic shock to be delivered to the body of the patient, such that a first of the two therapy electrodes can deliver a first phase of the biphasic shock with the other therapy electrode acting as a return, and the other therapy electrode can deliver the second phase of the biphasic shock with the first therapy electrode acting as the return. The connection pod electrically couples the plurality of ECG sensing electrodes 112 and the plurality of therapy electrodes 114 to the portable treatment controller 120, and may include electronic circuitry. For example, in one implementation the connection pod includes signal acquisition circuitry, such as a plurality of differential amplifiers to receive ECG signals from different ones of the plurality of ECG sensing electrodes 112 and to provide a differential ECG signal to the portable treatment controller 120 based on the difference therebetween. The connection pod may also include other electronic circuitry, such as a motion sensor or accelerometer by which patient activity may be monitored. A motion sensor may also be disposed in the portable treatment controller 120 to change the orientation of the display upon a change in the orientation of the portable treatment controller, to detect a drop or abuse event, etc.

In some embodiments, both the first therapy electrode 114a and the second therapy electrode 114b are disposed on the front of the patient's torso. For example, the first therapy electrode 114a may be located at external to the apex of the heart and the second therapy electrode 114b may be located along the parasternal line. Thus embodiments are not limited to a particular arrangement of therapy electrodes 114.

In some embodiments, the plurality of ECG sensing electrodes 112 are positioned and paired such that artifacts generated from electrical activity are decreased. In other embodiments, the electronic circuitry included in the portable treatment controller 120 may equalize artifacts measured at electrodes by changing a gain or impedance.

As shown in FIG. 1A, the medical monitoring and treatment device 100 may also include a user interface pod that is electrically coupled to the portable treatment controller 120. The user interface pod can be attached to the patient's clothing or to the harness 110, for example, via a clip (not shown) that is attached to a portion of the interface pod. Alternatively, the user interface pod may simply be held in a person's hand, or may be integrated into a watch 145 that communicates wirelessly with the portable treatment controller 120. In some embodiments, the user interface pod may communicate wirelessly with the user interface 108 of the ambulatory medical device controller 120, for example, using a Bluetooth®, Wireless USB, ZigBee, Wireless Ethernet, GSM, or other type of communication interface. The user interface pod typically includes one or more actionable user interface elements (e.g., one or more buttons, a fingerprint scanner, a touch screen, microphone, etc.) by which the patient, or a bystander can communicate with the portable treatment controller 120, and a speaker by which the portable treatment controller 120 may communicate with the patient or the bystander. In certain models of the LifeVest® Wearable Cardioverter Defibrillator, the functionality of the user interface pod is incorporated into the portable treatment controller 120, and the portable treatment controller 120 includes an LCD display.

The portable treatment controller 120 generally includes at least one processor, microprocessor, or controller, such as a processor commercially available from companies such as Texas Instruments, Intel, AMD, Sun, IBM, Motorola, Freescale and ARM Holdings. In one implementation, the at least one processor includes a power conserving processor arrangement that includes a general-purpose processor, such as an Intel® PXA270 processor and a special purpose processor, such as a Freescale™ DSP56311 Digital Signal Processor. The at least one processor of the portable treatment controller 120 is configured to monitor the patient's medical condition, to perform medical data logging and storage, and to provide medical treatment to the patient in response to a detected medical condition, such as cardiac arrhythmia.

The medical monitoring and treatment device 100 may include additional sensors, other than the ECG sensing electrodes 112, capable of monitoring the physiological condition or activity of the patient. For example, sensors capable of measuring blood pressure, cardiopulmonary vibration information, heart rate, heart sounds, thoracic impedance, pulse oxygen level, respiration rate, muscle activity (e.g., electromyographic or EMG sensors), tissue fluid, tissue inflammation, and the activity level or body position of the patient may also be provided.

For example, the medical monitoring and treatment device 100, may include one or more vibration sensors 116 to detect a patient's cardiac or pulmonary (cardiopulmonary) vibration information. For example, the cardiopulmonary vibrations sensors 116 can be configured to detect heart valve vibration values including any one or all of recurring sounds of a cardiac cycle that are separated and classified according to the activity associated with the vibration. The first heart sound (S1) is associated with the vibrational sound made by the heart during tensing of the mitral valve within a frequency range from 1 to 100 Hz. The second heart sound (S2) marks the beginning of diastole. The third heart sound (S3) is related to filling pressures of the left ventricle during diastole. The fourth heart sound (S4) is associated with atria contraction such as to overcome an abnormally stiff (e.g. ischemic) ventricle. From these heart vibration values (any of S1, S2, S3, and S4), certain electromechanical metrics may be calculated, including any one or more of electromechanical activation time (EMAT), percentage of EMAT (% EMAT), systolic dysfunction index (SDI), and left ventricular systolic time (LVST). The cardiac vibrations sensors 116 may also be configured to detect heart wall motion, for instance, by placement of the sensor in the region of the apical beat. The vibrations sensors 116 can include an acoustic sensor configured to detect vibrations from a subject's cardiac or pulmonary (cardiopulmonary) system and provide an output signal responsive to the detected vibrations of the targeted organ, for instance, being able to detect vibrations generated in the trachea or lungs due to the flow of air during breathing. The vibrations sensors 116 can also include a multi-channel accelerometer, for example, a three-channel accelerometer configured to sense movement in each of three orthogonal axes such that patient movement/body position can be detected. The vibrations sensors 116 can transmit information descriptive of the heart vibrations information or patient position/movement to a sensor interface for subsequent analysis, as described with reference to FIG. 2.

The tissue fluid sensor 118 can use radio frequency (RF) based techniques to assess fluid levels and accumulation in a patient's body tissue over preset intervals such as 12 h, 24 h or 48 h. For example, the tissue fluid sensor 118 includes a plurality of RF transceivers, such as antennas configured to transmit and receive RF waves towards and from a tissue of interest (e.g., the patient's lung). The RF waves of the tissue fluid sensors can have a frequency in the MHz to GHz range. The tissue fluid sensor 118 also includes one or more processors configured to analyze the characteristics of the received RF waves to generate an indication of fluid content in the tissue. For example, the fluid content indication (e.g., fluid volume and/or fluid accumulation location) in the patient's lung. Such an indication is typically used for diagnosis and follow-up of pulmonary edema or lung congestion in heart failure patients. The tissue fluid sensor 118 can transmit information descriptive of the tissue fluid levels to a sensor interface (e.g., sensor interface 212 described with reference to FIG. 2) for subsequent analysis. Examples of radio frequency circuitry that may be used as the tissue fluid monitor described in, for example, U.S. Pat. No. 8,989,837 entitled "Methods and Systems for Determining Fluid Content of Tissue," the content of which is incorporate herein by reference.

In various models of the LifeVest® Wearable Cardioverter defibrillator, the portable treatment controller 120 determines whether a treatable life-threatening cardiac arrhythmia is present based primarily on an analysis of the ECG signals obtained from the patient. Such an analysis may include, for example, QRS signal detection based upon digitized ECG signals, the morphology of the detected QRS signals and the patient's heart rate, axis analysis of patient's heart using vector cardiographic techniques, and the spectral analysis of various frequency components of patient's ECG signals, such as described in U.S. Pat. No. 5,944,669 (the "'669 patent"), which is hereby incorporated by reference herein. An arrhythmia detection component that is executable on the portable treatment controller 120 evaluates the various ECG metrics, as well as other metrics to determine a confidence level of whether a treatable arrhythmia exists, as described in detail with reference to FIGS. 9 and 10. Other metrics that are evaluated by the arrhythmia detection component typically include the signal to noise ratio of the ECG signals, the correlation between detected anomalies in the ECG signal and the presence of noise, a correlation between detected anomalies in the ECG signal and motion of the patient, as well as the general activity level of the patient. If the confidence level of the detected arrhythmia exceeds a determined threshold, the portable treatment controller classifies the ECG rhythm as a shockable cardiac arrhythmia rhythm and activates a treatment component configured to provide treatment to the patient.

Activation of the treatment component generally includes a charging of capacitors that are operatively coupled to the treatment electrodes and capable of storing sufficient energy to provide one or more defibrillating shocks to the body of the patient. The capacitors are typically disposed within the portable treatment controller and coupled to a power source, such as a battery, that is also typically disposed within the controller. In some embodiments, the capacitors, and/or the battery may be separate from the portable treatment controller; for example, the capacitors may be located on opposing sides of the patient's torso for better weight distribution and comfort. In response to detection of the treatable cardiac arrhythmia and the charging of the capacitors, the portable treatment controller generally issues an audible alarm or alert via a loudspeaker (not shown) on the portable treatment controller 120 and/or the user interface pod alerting the patient and any bystanders to the patient's medical condition. The alert is generally repeated one or more times during and after the charging of the capacitors and the continued detection of the arrhythmia. In the event that the detected arrhythmia continues, and even after the capacitors are fully charged to an energy level capable of providing one or more defibrillating shocks to the body of the patient, the portable treatment controller 120 instructs the patient to press and hold one or more buttons on the portable treatment controller 120 or on the user interface pod or watch 145 to indicate that they are conscious, thereby instructing the portable treatment controller 120 to withhold the delivery of one or more therapeutic defibrillating shocks. If the patient does not respond, the device presumes that the patient is unconscious or otherwise incapacitated and in need of treatment, and proceeds with the treatment sequence, culminating in the delivery of one or more defibrillating shocks to the body of the patient, as described in detail with reference to FIGS. 9 and 10.

Although various models of the LifeVest® Wearable Cardioverter Defibrillator can provide a defibrillating shock within 45 seconds from the detection of the onset of a detected cardiac arrhythmia such as VF, in some situations it can be advantageous to initiate, hasten, or delay, the administration of electrical therapy to a patient. Accordingly, a review of ECG data obtained from a number of patients was conducted to determine whether other forms of ECG analysis, and other physiological parameters of the patient could be used to determine whether to initiate, hasten or delay the administration of treatment.

As described below, a determination of appropriate energy pulse characteristics to convert a shockable VT/VF event can be improved by using vector values from ECG leads applied to a patient. FIG. 1B shows example derivation of a transform value 130 that represents at least one frequency component of ECG signals received from a monitoring and treatment device 100 worn by a patient 102. In the scenario shown in FIG. 1B, vector values are acquired from ECG sensing electrodes 112 (and thereby leads) applied to the patient 102 by the monitoring and treatment device 100. The vector values are then processed, potentially with other data, to determine an appropriate level of energy or other energy characteristics for one or more defibrillation shocks. A series of lettered boxes shown adjacent to the patient 102 represent one or more operations that the device 100 can perform in providing the appropriate level of energy or other energy characteristics for one or more defibrillation shocks. Shockable cardiac arrhythmia rhythm can include cardiac rhythms that are unable to sustain life in the patient. For example, the device can classify a VT rhythm as a shockable VT rhythm based on one or more factors. For example, the device includes a memory storing one or more parameters corresponding to the classification of a shockable VT or a shockable VF rhythm. In some instances, a prescriber, technician, or other professional can specify values or change values corresponding to these parameters to configure the device in its classification of shockable rhythms. Examples of such parameters can include heart rate, morphology, prior rhythm history of the patient, or an indication of a type of VT or VF rhythm, such as whether the rhythm is a fine VF rhythm, coarse VF rhythm, monomorphic VT, polymorphic VT, among others.

The electrodes in the device 100 are arranged such that the electrical depolarization signal generated by the beating heart arrives at different leads in a substantially orthogonal manner. In particular, the heart tissue depolarizes in a wave that defines the coordinated beat of the heart, so that electrical potential sensed by electrodes follows that order of depolarization to zones on the patient's skin that are located closest to the depolarizing zone. Thus, by having the ECG sensing electrodes 112 in appropriate locations, the phases of the relevant signals can be made near orthogonal (e.g., leading or trailing by about 90 degrees in the cycle) or out of phase (180 degrees from each other in the cycle). For example, leads may receive signals in a front-back configuration on the patient's 102 torso, or side-to-side, where each pair can be 90 degrees from another pair. In this regard, in the LifeVest® wearable cardioverter defibrillator, the two ECG sensing electrodes 112, referenced as a side-side (SS) lead and a front-back (FB) lead are substantially orthogonal. The combination of ECG data from different ECG sensing electrodes 112 may be represented as a vector value in a three dimensional space. Such representations are termed vectorcardiograms (VCG), and represent the electrical activity of the heart as the motion of a vector in three-dimensional space.

The number of ECG sensing electrodes 112 can vary, though two or more are generally preferred to obtain a vectorized signal. The signals provided by two such leads are shown schematically in the box labeled (A) 132, as multiple vectors unassociated with each other, and at box (B) 134 as vectors represented having a common base, and each having a particular magnitude and direction at a particular point in time in a cardiac cycle. As shown, the signals from the leads are substantially, though not perfectly, orthogonal to each other, where a particular angle may be selected to be a zero degree point for the cardiac cycle (i.e., for each heartbeat).

At the box labeled (B) 134, the device 100 has adjusted the signals to make them orthogonal to each other by known transformation techniques to create an XYZ representation for the patients 102 signal. For example particular signals may be projected onto orthogonal vector representations in an XYZ representation. The representation thus shows, in an orthogonal manner, the temporal change in surface potentials for the heart in a manner that is more readily susceptible to analysis and comparison to prior analysis of prior cardiac events. Use of a vector representation may permit better visibility into the condition of the heart during VF, when the hearts motion and electrical activity is not organized. For example, the analysis may provide a better indication of the actual physical qualities of the heart during VF, as opposed to random changes that may have little or no helpful information.

In some implementations, an optimal angle for projecting the values onto an orthogonal representation can be determined. For example, a determination may first be made to identify an angle for a projection that provides a maximum amplitude of a projection for a particular sampling interval. A maximum amplitude can then be identified in the interval from that angle. And the values may then be geometrical projected onto the coordinates of the orthogonal representation. For each sampling interval then, the process selects a configuration that provides a maximum amplitude, so that the signal is normalized from one sample to the next.

At the box labeled (C) 136, the Complex Discrete Fourier Transform (DFT) may be applied to all components of the produced vector to transform the data from the time domain to the frequency domain. Such transform may occur in multi-dimensional space and produce data that is interpretable in a complex frequency spectrum. Such transformation may occur by standard mathematical transform methods and produce data that is interpretable in standard manners.

A multidimensional DFT is represented as:

$$X_k = \sum_{n=0}^{N-1} e^{-2\pi i k(n/N)} x_n$$

Therefore, the multidimensional DFT transforms an array $x_n$ with a d-dimensional vector of indices $n=(n_1, \ldots, n_d)$ by a set of d nested summations (over $n_j=0 \ldots N_j-1$ for each j), where the division n/N, defined as $n/N=(n_1/N_1, \ldots, n_d/N_d)$, is performed element-wise. The multidimensional DFT is therefore a composition of a sequence of d sets of one-dimensional DFTs, performed along one dimension at a time. The order in which the individual one-dimensional DFTs are performed does not affect the results of the computation. Therefore, a multi-dimensional DFT can be computed, for example, using a row-column process, by performing a sequence of one-dimensional FFTs along one dimension (e.g., row-wise), followed by a sequence of one-dimensional FFTs along another dimension (e.g., column-wise). In some implementations, the column-wise FFTs can precede the row wise FFTs. This process can be extended for more than two dimensions for higher-dimension data.

In some implementations, the VCG may be described using a spherical coordinate system. For example, the spherical coordinates (r, θ, φ) can be used to represent radial distance r, polar angle θ (theta), and azimuthal angle φ (phi). The symbol ρ (rho) is often used instead of r. In some cases, Cartesian coordinate systems may not represent the activity of the electrical vector of the heart with sufficient resolution. However, because the activity is rotational in nature (with respect to a fixed origin), representing the VCG using a polar or spherical coordinate system may be of benefit in such cases.

In some implementations, because electrical activity is often impacted by the physical structure of the heart itself, it may be beneficial to align the spherical coordinate system with the physical structure of the heart. This can be accomplished, for example, by imaging of the heart at the time of VCG acquisition. By using a portable ultrasound system, such as the NanoMaxx® with P21N® probe (by Sonosite of Bothel Wash.), the location of the heart's apex, along with the angular axis of the heart can be determined. In some implementations, an inertial sensor system, such as the Analog Devices ADIS164362 Tri-Axis Gyroscope, Accelerometer, may be used to determine the position and angle of the ultrasound probe with respect to the location of the VCG apex electrode. The relative locations and angles of the heart's axis and apex position with respect to the VCG electrode can be stored along with the VCG. In some implementations, a rotational transform may align the zero polar and azimuthal angles of the spherical coordinate system of the VCG with the physical axis of the heart.

In some implementations, for example, when the VCG is represented in a spherical coordinate system, a Spherical Fourier Transform can be used as the transform. Examples of Spherical Fourier Transforms are described by Wang, et al., in "Rotational Invariance Based on Fourier Analysis in Polar and Spherical Coordinates," IEEE Transactions on Pattern Analysis and Machine Intelligence, VOL. 51, NO. 9, September 4009, and in Wang et al., "Fourier Analysis in Polar and Spherical Coordinates," Internal Report, Albert-Ludwigs University Freiburg, 4008. Spherical Fourier analysis can be defined as the decomposition of a function in terms of eigenfunctions of the Laplacian with the eigenfunctions being separable in the corresponding coordinates. The VCG can therefore be decomposed into wave-like basic patterns that have clear radial and angular structures. In some implementations, this decomposition can be an extension of Fourier analysis and can, therefore, be called Fourier analysis in the corresponding coordinates. In some cases, the radius of the VCG vector may undergo very little change, and the relevant changes occur primarily in the rotational dynamics of the heart's electrical vector. In such cases, using conventional Cartesian spectral analysis can cause the rotational dynamics to be inadequately represented by the rectangular representation.

Other frequency domain transformation methods may be used instead of or in addition to DFT. In some implementations, fast Fourier transform (FFT) processes can be used in computing the multidimensional DFTs. The mathematical transform can be determined using Fourier transform, discrete Fourier transform, Hilbert transform, discrete Hilbert transform, wavelet transform, and discrete wavelet methods.

At the box labeled (D) 138, the frequency domain data is used to compute a transform value representing at least one of the frequency components of the ECG signal. For example, the transform value is 16.2 mV-Hz. In some implementations, as shown by the box labeled (E) 140 the transform value can be further transformed to an equivalent value that is expressed in a different manner, and still be considered a transform value. In some implementations, the transform value may be the area of an amplitude spectrum (ASA or AMSA, and simply referred to as AMSA hereafter). More generally, the computation may be of a value that represents a weighted amplitude of the signal, and generated from the signal after a frequency domain transformation so as to provide an indication of the signal weight in the frequency domain.

Figure 1C:
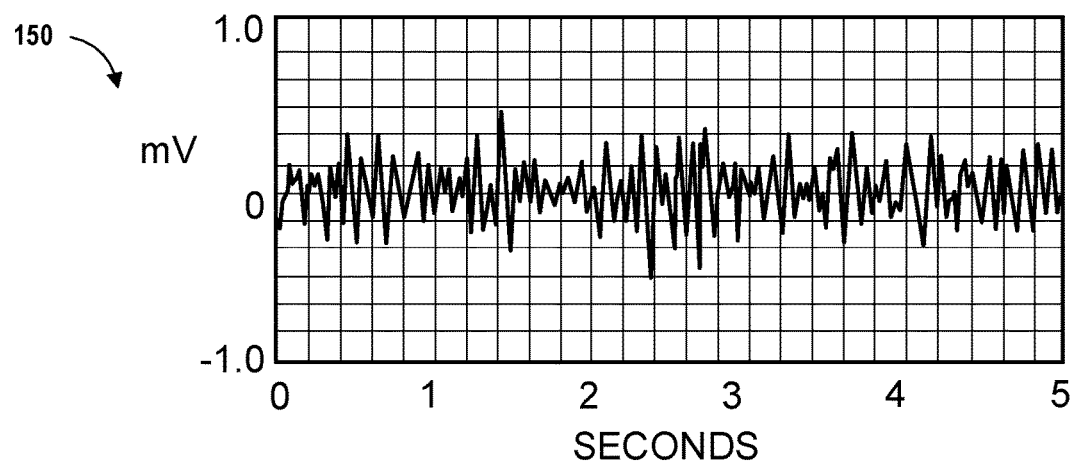
FIG. 1C illustrates examples of waveforms that can be used to generate a transform value.
Figure 1C:
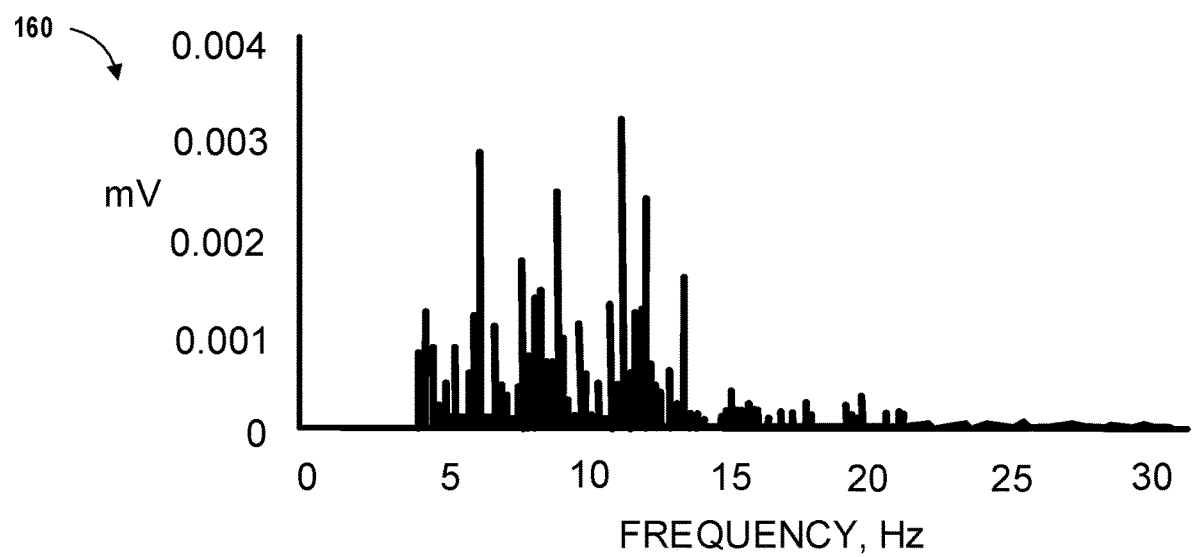

An example calculation of a transform value is as follows using ECG signals as illustrated in FIG. 1C. In this calculation, it is assumed that an ECG signal (such as ECG signal 150 in FIG. 1C) was selected to be between 4 and 48 Hz to minimize low frequency artifacts produced by precordial compression and to exclude electrical interference of ambient noise at frequencies >48 Hz. Peak-to-peak trough VF amplitudes (or magnitudes) were obtained and the average was calculated for a specific ECG interval.

A power spectrum (such as power spectrum 160 in FIG. 1C) can be obtained by squaring the amplitude (or magnitude) of each frequency component obtained from a fast-Fourier transform of the ECG signal. A median frequency is selected to represent a frequency at which half of the power of the spectrum is above and half below the median frequency. The median frequency can be represented by equation (1):

$$MF = \Sigma Fi \times Pi / \Sigma Pi \quad (1)$$

The parameter $Fi$ is the $i^{th}$ frequency component and $Pi$ is the relative power at $Fi$. The transform value can be calculated from the resulting amplitude frequency spectrum using equation (2):

$$\text{Transform value} = \Sigma Ai \times Fi \quad (2)$$

The parameter $Ai$ is the amplitude or magnitude at the $i^{th}$ frequency $Fi$.

In implementations, the transform value can be derived by changing the multiplier in equation (2) from $Fi$ to another value. For example, $Fi$ may be replaced by an $n^{th}$ exponential of $Fi$ (e.g., Fi-squared, or square-root of Fi) as illustrated by equation (3).

$$\text{Transform value} = \Sigma Ai \times Fi^n \quad (3)$$

In some implementations, instead of or in addition to Fi, a plurality of weighting factors, e.g., represented as vector $\mu$ be introduced in the calculation of the transform value. The values of the vector $\mu$ may be in a linear or nonlinear relationship with the amplitude or magnitude vector A as illustrated by equation (4).

$$\text{Transform value} = \Sigma Ai \times \mu_i \quad (4)$$

For example, where Fi was in a linear relationship with the frequency range of the spectrum, $\mu$ may be in a nonlinear relationship with the frequency range. In some implementations, $\mu$ may have an exponential distribution over the range of the power spectrum.

In implementations, the $\mu$ values may be distributed in a pre-established manner to corresponding amplitude or magnitudes values A over the range of the spectrum. For example, a $\mu$ value may be in a pre-established linear or nonlinear relationship with a corresponding magnitude value A, such that when Ai is in a high end of a range, $\mu i$ may also be in a high end of its range. For instance, if $\mu$ is normalized in a range of 1 to 100, $\mu i=1$ for low or near-zero Ai values, and µi=100 for maximum or peak Ai values within the range of the spectrum. Conversely, a µ value may be in an inverse relationship with a corresponding magnitude value A, such that when Ai is in a high end of a range, pi may be in a low end of its range. In implementations, µ may have a distribution selected in accordance with a type of statistical noise distribution experienced by the system. For instance, µ may have a Gaussian distribution over the range of the spectrum. For example, the parameter µ is selected as a design choice when implementing the AMSA transform value in the device. As described above, the design choice can be based on a desire to use a different multiplier than the frequency component (Fi), e.g., to develop a unique transform value for the device. In some examples, the design choice can be based on using a standard noise distribution for µ in order to better reflect a noise environment in which the device operates.

Referring again to FIG. 1B, at the box labeled (E) 140, the transform value can be combined with other factors that are known to affect a success rate or energy characteristics of defibrillating shocks applied to a patient. For example, considerations about how long the patient has been in cardiac arrest, how many prior shocks have been applied, the relative success level of those prior shocks (e.g., did they fully defibrillate or partially defibrillate, and for how long), trans-thoracic impedance, tissue fluid level(s) as determined by a tissue fluid monitor, heart vibrational and/or electro-mechanical parameters calculated from vibrational sensors and/or ECG data, and other possible inputs. Such values be normalized to a common representation (e.g., a parameter-less number) and weighted according to what their respective contribution is determined to be for calculating the energy characteristics of a defibrillation shock. Each of the input signals can be converted into a common format for all the signals (e.g., a particular dimensionless value) and as part of that process or as an additional step, each signal may be weighted so that a composite indication can be generated that properly incorporates each relevant signal at a level that such signal contributes to the calculation of the energy characteristics of a defibrillation shock.

In one set of experiments, ECG data from a number of patients was analyzed using a variety of different ECG analysis techniques. Of the data samples evaluated, the ECG data from approximately fifteen patients was analyzed in detail. The vast majority of those patients initially exhibited VT, which then degraded to VF. A spectral analysis of the VF rhythm waveforms obtained from the electrocardiograms (ECGs) of the patients showed that in a majority of the patients, the AMSA of the VF rhythm waveform declined by about one third from a value of approximately 35 mV*Hz at the detected onset of VF rhythm to a value of approximately 25 mV*Hz approximately 45 seconds after the detected onset of VF. In general, subjects with an AMSA value of about 21 mV*Hz or more have a statistically good chance of survival with typical interventions, such as defibrillation, while those with an AMSA value of approximately 12 mV*Hz have about a 50% chance of survival, and those with AMSA values below about 7 mV*Hz are statistically unlikely to survive. Further details regarding the success of defibrillation relative to the transform value (e.g., AMSA value) and the energy level of the defibrillation shock are included in the description of FIGS. 3 and 4.

In accordance with the experiments and analysis, a non-invasive wearable medical monitoring and treatment device is provided that analyzes ECG signals received from a patient using QRS signal detection, morphology of detected QRS signals and the patient's heart rate, axis analysis, and spectral analysis of various frequency components of the patient's ECG signal as described in the '669 patent, but which in addition monitors transform value (e.g., AMSA) of the VF waveform obtained from the digitized ECG signals, to determine optimal parameters (e.g., timing, waveform, intensity, etc.) for the application of electrical therapy, such as defibrillation, and whether to recommend another type of intervention, such as CPR. In addition to the transform value, one or more other metrics that are indicative of the general viability of the heart, or indicative of the chances of success of a therapeutic intervention to terminate the lethal arrhythmia can be used. Examples of such metrics include quantitative waveform measures (QMM), median slope (MS), and logarithm of the absolute correlations (LAC). Other frequency-based or transform-based metrics, such as metrics based on wavelet transforms or Hilbert transforms, can also be used in determining types and/or amount of intervention.

An advantage to the use of the transform value of the VF rhythm as a metric to optimize the administration of electrical therapy, such as defibrillation, is that transform values may be determined from an ECG that is obtained during the performance of chest compressions, and further, the subject's ECG may be filtered (e.g., using a band pass filter with a pass band between approximately 2 to 40 Hz) to remove artifacts relating to chest compressions without impacting the predictive capability of the transform values calculated therefrom. In accordance with embodiments of the present technology, the medical monitoring and treatment device may also monitor the patient's ECG signals to detect the onset of VT, and provide therapy to the patient, in the form of a low-level electrical shock to induce conversion to sinus rhythm, or in the form of pacing, to reduce the possibility of VF.

Figure 2:
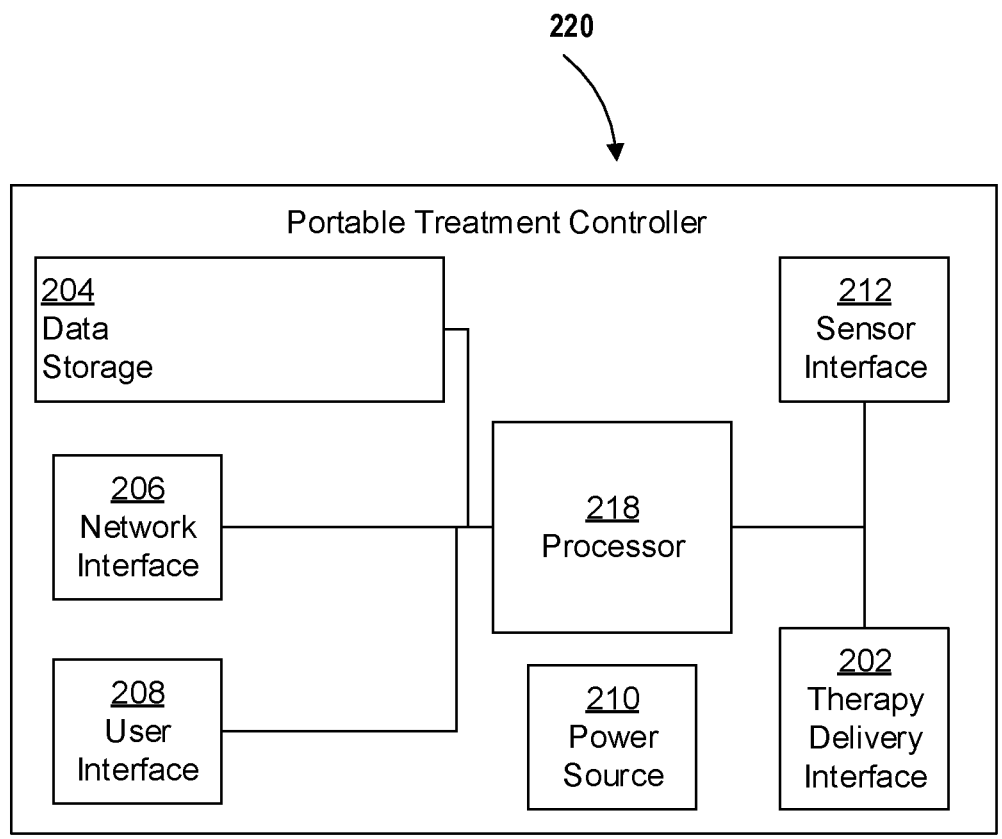
FIG. 2 is a functional block diagram of one example of a portable treatment controller that may be used in the medical monitoring and treatment device of FIGS. 1A and 1B.

FIG. 2 illustrates a portable treatment controller 220 that is configured to perform the critical functions of monitoring physiological information, such as ECG signals for abnormalities and initiating treatment of detected abnormalities in accordance with an aspect of the present technology. As shown, the portable treatment controller 220 includes at least one processor 218 specifically configured to perform one or more of the features described herein. In one implementation, the at least one processor 218 includes a power conserving processor arrangement that includes a first processor, such as an Intel® PXA270 processor and a second processor, such as a Freescale™ DSP56311 Digital Signal Processor. Such a power conserving processor arrangement is described in co-pending application Ser. No. 12/833,096, titled SYSTEM AND METHOD FOR CONSERVING POWER IN A MEDICAL DEVICE, filed Jul. 9, 2010 which is incorporated by reference herein in its entirety. The at least one processor 218 of the portable treatment controller 220 is configured to monitor patient's ECG signals, to perform medical data logging and storage, to detect various cardiac arrhythmias, and to provide lifesaving defibrillation treatment to a patient suffering a treatable form of cardiac arrhythmia, such as Ventricular Fibrillation (VF) or Ventricular Tachycardia (VT).

The portable treatment controller 220 further includes a sensor interface 212, a therapy delivery interface 202, data storage 204, a communication network interface 206, a user interface 208, and a power source 210, such as a battery. In the illustrated example, the power source 210 is a rechargeable 3-cell 2200 mAh lithium ion battery pack that provides electrical power to the other device components with a minimum 24-hour runtime between charges. Such a battery has sufficient capacity to administer one or more therapeutic shocks and the therapy delivery interface 202 has wiring suitable to carry the load to the therapy electrodes 114. Moreover, in the example shown, the battery has sufficient capacity to deliver up to 5 or more therapeutic shocks, even at battery runtime expiration.

The sensor interface 212, the therapy delivery interface 202, the data storage 204, the network interface 206, and the user interface 208 are coupled to the at least one processor 218 by, for example, a bus. In the example shown, the data storage 204 includes a computer readable and writeable nonvolatile data storage medium configured to store non-transitory instructions and other data. The medium may, for example, be optical disk, magnetic disk or flash memory, among others and may be permanently affixed to, or removable from, the portable treatment controller 220.

The user interface 208 shown in FIG. 2 includes a combination of hardware and software components that allow the portable treatment controller 220 to communicate with an external entity, such as a user. The components are configured to receive information from actions such as physical movement, verbal intonation or thought processes. In addition, the components of the user interface 208 can provide information to external entities. Examples of the components that may be employed within the user interface 208 include keyboards, mouse devices, trackballs, microphones, electrodes, touch screens, printing devices, display screens speakers, computer-enabled glasses, watches, or earpieces.

As shown in FIG. 2, the portable treatment controller 220 includes several system interface components 202, 206 and 212. Each of the system interface components is configured to exchange, i.e., send or receive data, with specialized devices that may be located within the portable treatment controller 220 or elsewhere. The components used by the interfaces 202, 206 and 212 may include hardware components, software components or a combination of both. In the instance of each interface, the components physically and logically couple the portable treatment controller 220 to one or more specialized devices. The physical and logical coupling enables the portable treatment controller 220 to both communicate with and, in some instances, control the operation of specialized devices. The specialized devices may include physiological sensors, therapy delivery devices, and computer networking devices.

According to various examples, the hardware and software components of the interfaces 202, 206 and 212 employ a variety of coupling and communication techniques. In some examples, the interfaces 202, 206 and 212 use leads, cables or other wired connectors as conduits to exchange data between the portable treatment controller 220 and specialized devices. In other examples, the interfaces 202, 206 and 212 communicate with specialized devices using wireless technologies such as radio frequency or infrared technology. The software components included in the interfaces 202, 206 and 212 enable the at least one processor to communicate with specialized devices. The software components may include elements such as objects, executable code and populated data structures. Together, the hardware and software components provide interfaces through which the at least one processor 218 can exchange information with the specialized devices. Moreover, in at least some examples where one or more specialized devices communicate using analog signals, the interfaces 202, 206 and 212 can include components configured to convert analog information into digital information, and vice-versa.

As discussed above, the system interface components 202, 206 and 212 shown in the example of FIG. 2 support different types of specialized devices. For instance, the components of the sensor interface 212 couple the at least one processor 218 to one or more physiological sensors such as vibration sensors (e.g., vibration sensors 116 described with reference to FIG. 1A), tissue fluid sensors (e.g., tissue fluid sensors 118 described with reference to FIG. 1A), body temperatures sensors, activity sensors (e.g., accelerometers), pulse oxygen sensors, thoracic impedance sensors, blood pressure sensors, acoustic sensors, respiration monitors, muscle activity (electromyographic or EMG) sensors 216 (other than ECG sensors), and dry-capacitive ECG sensing electrodes 112. In some embodiments, other types of ECG sensing electrodes may be used, such as gelled or non-gelled adhesive-backed ECG sensing electrodes, as the present technology is not limited to any particular type of ECG sensing electrode. Signal processing circuitry within the sensor interface 212 buffers, amplifies, and in some embodiments, filters the subject's ECG signal, and samples of the processed ECG signal are digitized by an A/D converter and provided to the at least one processor 218. The sensor interface 212 can typically include one or more amplifiers to buffer, amplify, and/or filter the ECG signals of the subject and an Analog to Digital (A/D) converter to sample and digitize the patient's ECG signal and provide the digitized samples of the ECG signal to the at least one processor, although one or more of the functions could alternatively be performed elsewhere in the portable treatment controller 220.

The at least one processor 218 can perform the processes described with reference to FIGS. 9 and 10. For example, the at least one processor 218 analyzes the digitized ECG signals to determine whether a normal cardiac rhythm is present, and if not, to determine whether a cardiac condition that is treatable by defibrillation (such as VT or VF) is present. Information from the digitized ECG signals that is analyzed can include the morphology of detected QRS signals and the patient's heart rate, axis analysis, and spectral analysis of various frequency components of the patient's ECG signal as described in the '669 patent. The at least one processor 218 may display the digitized ECG signal on a display associated with the user interface 208. In response to the at least one processor 218 determining that a treatable cardiac condition is present, the processor 218 transforms the time domain samples of the subject's ECG signal to the frequency domain, for example, by using a fast Fourier transform (FFT), and calculates one or more metrics that are based upon a spectral analysis of the transformed ECG signal. In accordance with an aspect of the present technology, the metrics that are calculated by the at least one processor 218 include transform values which are indicative of the probability of successful defibrillation (as described with reference to FIG. 4C) and the metabolic state of the patient's myocardium, although other metrics, such as the area of the power spectrum (PSA) could alternatively be used.

The components of the therapy delivery interface 202 couple one or more therapy delivery devices, such as capacitors and defibrillator electrodes, to the at least one processor 218. In addition, the components of the network interface 206 couple the at least one processor 218 to a computer network via a networking device, such as a bridge, router or hub. The network interface 206 may support a variety of standards and protocols, examples of which include USB, TCP/IP, Ethernet, Wireless Ethernet, Bluetooth, ZigBee, M-Bus, IP, IPV6, UDP, DTN, HTTP, FTP, SNMP, CDMA, NMEA and GSM. To ensure data transfer is secure, in some examples, the treatment controller 220 can transmit data via the network interface 206 using a variety of security measures including, for example, TSL, SSL or VPN. In other examples, the network interface 206 includes both a physical interface configured for wireless communication and a physical interface configured for wired communication.

Figure 3:
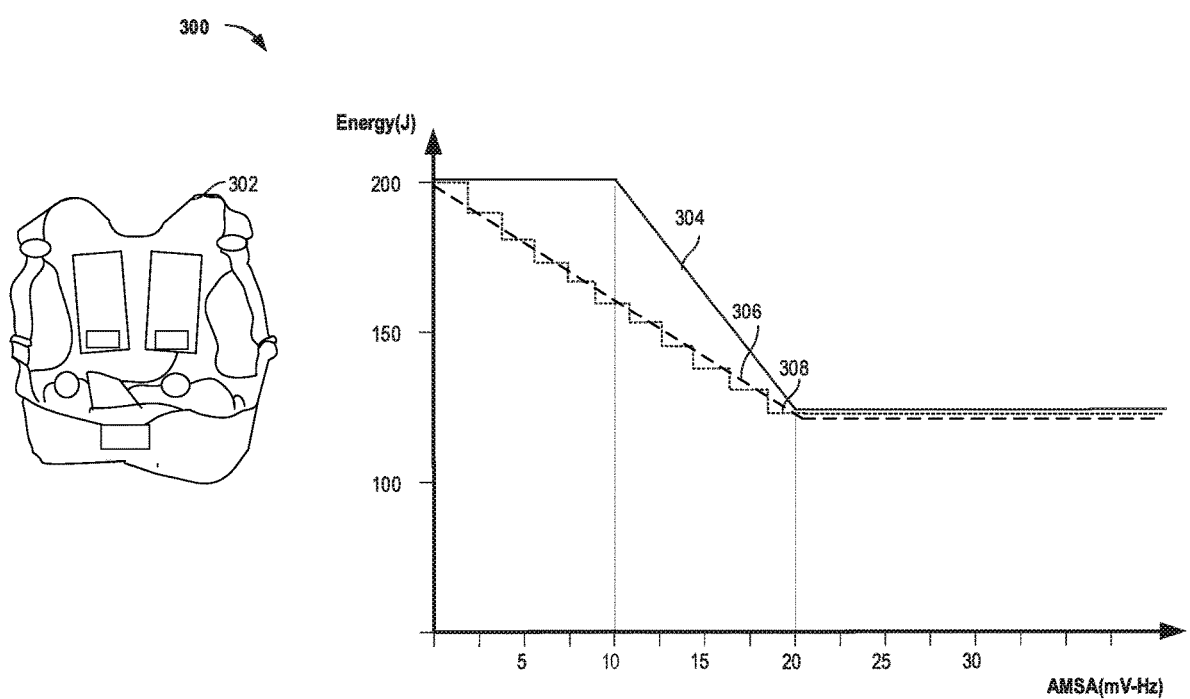
FIG. 3 shows a relationship between AMSA and shock energy that may be implemented by a wearable defibrillator.

FIG. 3 shows a graph 300 illustrating a relationship between a transform value (in this example, AMSA) and shock energy that may be implemented by a wearable defibrillator 302 (e.g., medical monitoring and treatment device 100 described with reference to FIG. 1A). The graph 300 shows identified relationships between AMSA transform values (expressed as mV-Hz according to common practice) and energy (expressed in Joules, as is also common practice) levels that have been determined to be needed to successfully defibrillate a patient at such corresponding AMSA transform values (e.g., above a predetermined predicted likelihood of success value). The values shown here may be programmed into a medical device like a defibrillator, where the AMSA value is treated as an independent variable (along with potentially other inputs, such as TTI), and the energy level is the dependent variable. In particular, an AMSA value or similar value (e.g., that is based on amplitudes in an ECG signal for a patient) may be computed from a patient's ECG data, and the medical device may adjust an energy level based on the computed AMSA value (and perhaps based on additional values, such as by blending the multiple inputs together in a weighted manner). The energy value may be applied automatically in charging capacitors for delivering a shock to a patient, or may be displayed or otherwise presented to a rescuer, with the rescuer able to override the suggested energy level with a manually entered energy level, followed by the rescuer choosing to deliver the shock.

Three example relationships are shown between AMSA transform values and energy output values in this example. Generally, each of the representations indicates that the energy needed to achieve a successful defibrillation falls as AMSA rises. The three examples show programming for a wearable defibrillator 302 by which the relationship between computed AMSA transform values and the energy computed by the wearable defibrillator 302 has different partially-linear relationships with AMSA (though non-linear relationships may also be employed). Such relationships may be determined by analyzing data collected by defibrillators in-the-field for past rescue events, and identifying AMSA for patients from such events (for both successful and unsuccessful delivered shocks), energy levels for such events, and defibrillation outcomes. Standard statistical techniques can then be applied to determine relationships between AMSA and energy for successful defibrillation and unsuccessful defibrillation. Other factors, as indicated in more detail below, may also be used in determining appropriate energy levels, such as trans-thoracic impedance (TTI), patient body size (e.g., weight or surface area, whether actual or estimated) and pharmacological history for the patient, either outside of the present VF episode or as part of the episode.

Stepped trace 308 generally shows increasing energy with decreasing AMSA transform values. The increases in energy may be stepped, such as in 3, 4, 5, or 30 Joule steps at appropriate AMSA transform values (every 0.5, 3, 4, 5, 4, or 5 steps of AMSA transform value). Such a trace 308 may be implemented by formula or look-up table, where the look-up table correlates the particular discrete values for AMSA shown here to an output for the multiple discrete levels of energy shown here.

In certain implementations, the energy may be flat for a range of AMSA transform values, but linearly changing for another range of AMSA transform values. For example, the energy can be flat at high and low AMSA transform values, and sloped in the middle. Trace 304 shows such a relationship for energy that will be computed by the defibrillator as changing by such a flat-slope-flat function. In this example, energy is consistent for a large range of AMSA transform values and then changes linearly for a mid-range of AMSA transform values, and is steady again for another range of AMSA transform values. Trace 306 is similar to trace 304 in that it has a sloped portion and a flat portion. However, trace 306 is sloped starting immediately at low AMSA levels until it flattens at a particular AMSA transform value (here, 40 mV-Hz).

Even though the graph 300 illustrates a relationship between AMSA and shock energy, in some implementations, the wearable defibrillator 302 can use AMSA value to modify other defibrillation shock parameters. Examples of such therapeutic and/or shock delivery parameters include, but are not limited to: peak defibrillation current or energy values, peak-to-peak defibrillation current or energy values first phase average defibrillation current or energy, defibrillation current or energy waveform duration, defibrillation peak voltage, defibrillation current or energy waveform rise or fall-time, defibrillation current or energy tilt values, defibrillation average current or energy values, and defibrillation root mean square (RMS) current or energy values. Other defibrillation current, voltage, and/or energy parameters may be modified based on the transform values described herein.

The particular traces shown here are provided for explication only, and other relationships may be programmed into a medical device such as a defibrillator, and the computation of appropriate energy may be based on multiple factors, in addition to an AMSA or similar value derived from ECG data. For example, a relationship may include both linear and non-linear portions if such is what data from past usage indicates is the best approach to having future defibrillators select output energy for shocks. The computation of output energy may depend on multiple inputs, as described with reference to FIGS. 4A-4C. For example, in addition to AMSA or other ECG amplitude-related criterion, the relationship between inputs and energy output may be determined in a variety of manners, including multi-dimensional regression analysis. The multi-dimensional regression analysis can be represented by a data structure or a formula for computing the energy output of the wearable defibrillator 302. The graph 300 and/or the multi-dimensional regression analysis for computing the energy output can be used during defibrillation treatments as described with reference to FIGS. 9 and 10.

Figure 4A:
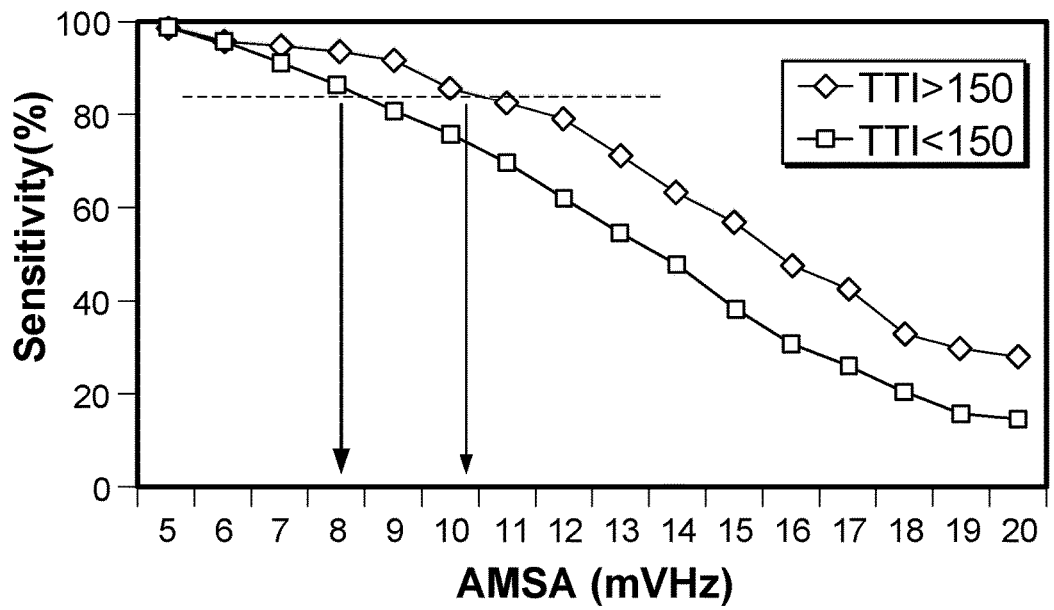
FIGS. 4A and 4B are graphs showing relationships between sensitivity and specificity, and AMSA threshold values for groups of patients.

FIG. 4A shows a plot of sensitivity (%) versus AMSA threshold (mv-Hz) for a first set of subjects having a trans-thoracic impedance (TTI) measured greater than 350 ohms, and a second set of subjects having a trans-thoracic impedance measured less than 350 ohms. The data shows the influence of TTI on the prediction accuracy of AMSA for shock success at different threshold values as presented in sensitivity and specificity. Such values may be incorporated with AMSA transform values so as to adjust an output energy for a defibrillator, where the output energy is both a function of AMSA (or other ECG based shock prediction value) and of TTI. A gain factor may be used to adjust for variations in TTI so as to maintain substantially equal levels of performance of AMSA with regard to assessing the likelihood of viability of future therapeutic actions, e.g., the viability of delivering a defibrillating shock. For example, referring again to FIG. 4A, the AMSA transform values for TTI <350 Ohms may be multiplied by a gain factor of 3.17 so that the two curves overlap more closely. In some implementations, a linear or non-linear regression analysis may be performed to determine the relationship between the optimal AMSA measure, which has as inputs to the regression equation the TTI measure, and the raw AMSA reading. In some implementations, the viability of a future therapeutic action may be expressed as a probability, e.g. 0-100%, and the probability may be adjusted by the TTI measure, for instance, using regression methods, table lookup or neural networks. In some implementations, complex relationships, such as depicted in FIG. 4B, may require table lookup or non-linear regression to be adjusted for effects of TTI.

The data was obtained by collecting data from defibrillators used in real rescue events from multiple emergency medical services in the United States through regular field case submission to ZOLL Medical Corporation, and where individual personal identifying information could not be determined from the gathered data. All reporting parties used ZOLL automatic wearable defibrillators that included current-based impedance compensation. The sampling rate for ECG data was 450 Hz, and analysis was performed on a selection of an episode of 4.05 seconds (512 data points) ending at 0.5 seconds before each shock attempt. Shock success was defined as an organized rhythm for a minimum of 50 seconds, starting 60 seconds after the delivered shock, and with a rate of 40 beats per minute or greater. A total of 3292 shocks (305 successful) form 580 patients with VF were included in the analysis. AMSA. The TTI was measure at shocking pads placed on each respective subject.

As shown by the comparative data, a patient's TTI affects the predictability of AMSA by shifting the threshold upward for a given sensitivity or specificity value. AMSA transform value was significantly higher when the TTI was greater than 350 ohm (11.6±8.9 vs. 9.8±7.1, p=0.002) as compared with those shocks with TTI less than 350 ohm. The AMSA threshold value was increased from 8.2 mVHz to 30.3 mVHz when sensitivity was set to 85%. Such information can be used to provide a real-time adjustment mechanism, like those discussed above, that adjusts an AMSA threshold for predicting likelihood of shock success or otherwise taking into account the real-time measured TTI so as to affect the reported likelihood in a manner that makes it more accurate.

Figure 4B:
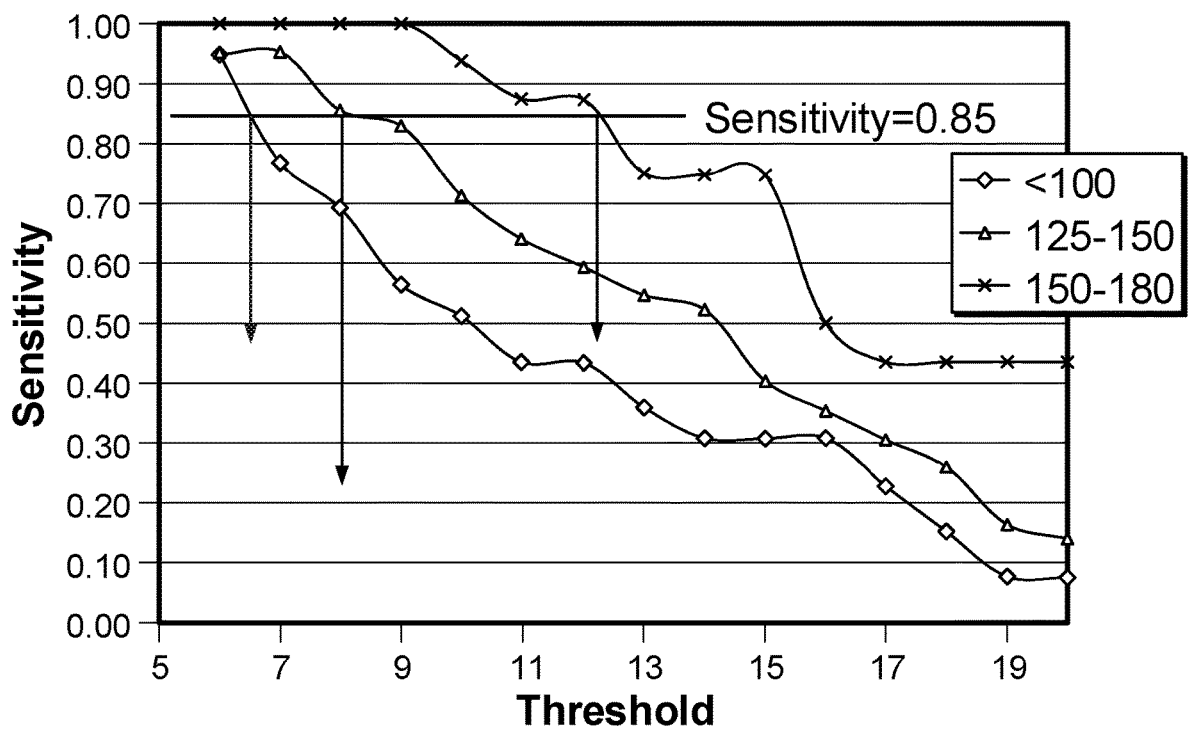

FIG. 4B shows a plot of specificity (%) versus AMSA threshold (mv-Hz) for a first set of subjects having a trans-thoracic impedance measured less than 350 ohms, a second set of subjects having a trans-thoracic impedance greater than 350 ohms. The tested subjects and data collection were the same as for the graph in FIG. 4A. As shown by the comparative data, AMSA threshold generally increases, for a given specificity, with increasing trans-thoracic impedance. For example specificity at a threshold of 85% was 31.8 mVHz for TTI<150 ohms, and 34.2 mVHz for TTI>150 ohms. Again, analysis of such data may be used in programming devices to provide predictions of likelihood of shock success, or to disable or enable the ability to shock a particular patient, based on calculated AMSA transform values.

Thus, in an implementation, the data structure can be established, and when a shockable rhythm is determined to exist for a patient (e.g., via ongoing analysis of ECG data from the patient), AMSA and other inputs or signals can be computed. Those inputs may then be used to compute an energy level to charge the defibrillator capacitor or capacitors to, in addition to other computations (e.g., a computation of a likelihood that a shock, if currently delivered, will succeed in defibrillating the patient).

The likelihood of shock success can depend upon a number of factors, relationships between or among factors, etc. For example, shock energy levels, delivery techniques, etc. may be defined based upon one or more quantities that use AMSA transform values. For example, AMSA transform values may be used to define regions that employ different energy levels, delivery techniques, etc. such as escalating energy levels for subsequent shocks.

In one study data was collected and analyzed from 3219 shocks from 543 patients with VF. ECG recordings, sampled at 450 Hz, were digitized and reviewed. Episodes of approximately two seconds (e.g., 4.05 seconds or 512 data points) that terminated a half second before a shock attempt were analyzed. Shock success was defined as an organized rhythm that was present for a minimum of 50 seconds, started within 60 seconds after the shock, and had a rate of 40 beats per minute or larger.

Using an escalating defibrillation energy protocol (with energy levels stepping from 320 Joules (J) to 350 J and to 400 J), shock success increased with each step for AMSA transform values of 32 mV-Hz or greater (e.g., 50.0% success for 320 J, 64.6% success for 350 J and 82.5% shock success for 400 J). For instances of lower AMSA transform values, below 32 mV-Hz, shock success rates did not significantly improve for the escalation steps (e.g., 9.3% success for 320 J, 32.4% for 350 J and 30.4% for 400 J). Through data analysis (e.g., using multivariable logistic regression), shock success for higher AMSA transform values (e.g., 32 mV-Hz and above) can depend upon the energy level (e.g., higher energy levels may demonstrate improved success) while lower AMSA transform values (e.g., below 32 mV-Hz) may solely depend on the AMSA transform values and be somewhat independent of escalating energy levels.

Figure 4C:
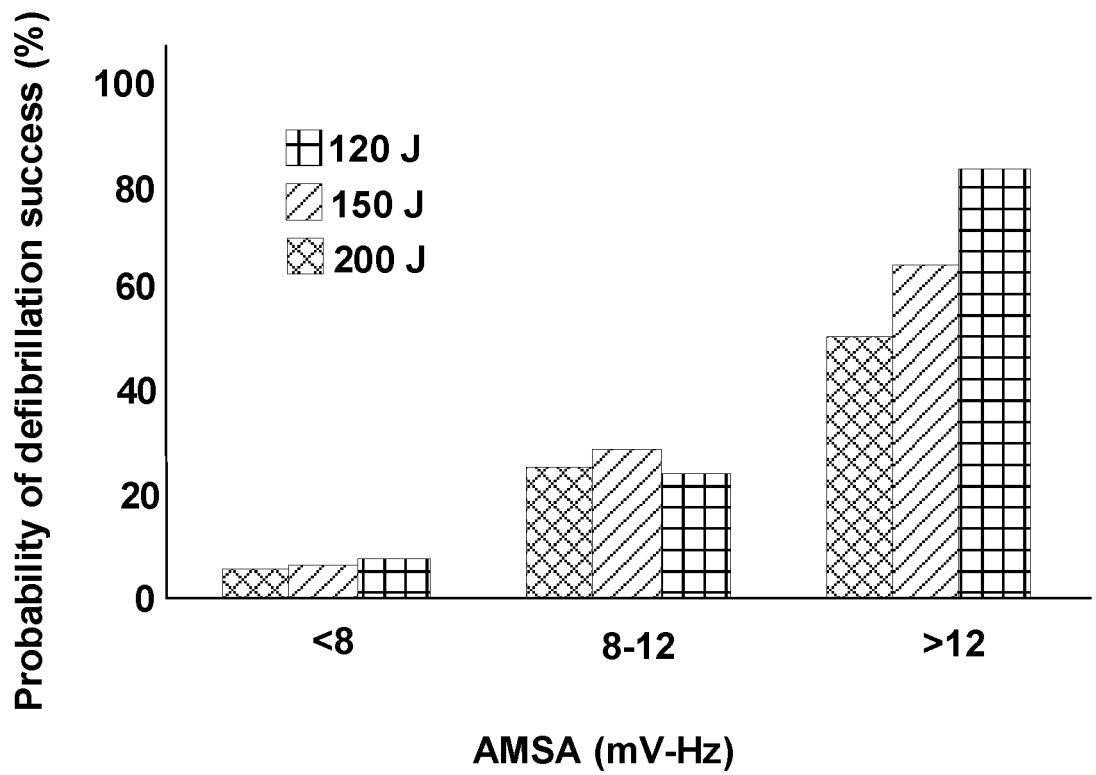
FIG. 4C is a graph showing relationships between AMSA transform values and the probability of defibrillation success.

Referring to FIG. 4C, for AMSA transform values larger than 32 mV-Hz, improvement in the probability of success is graphically depicted. One or more regions may be defined, for example using an AMSA transform value, and different shock protocols can be employed for each region. A single AMSA transform value (e.g., 32 mV-Hz) can define the upper boundary of a lower AMSA transform value region (e.g., values below 32 mV-Hz) and also provide the lower boundary of another region that includes equivalent and larger AMSA transform values (e.g., values of 32 mV-Hz and above). When operating within the first region (e.g., for AMSA transform values below 32 mV-Hz), a fixed low energy level protocol can be employed (e.g., the energy level used for an initial shock is also used for subsequent shocks). For operating in the second region (e.g., when an AMSA value of 32 mV-Hz or larger is measured from a patient), an escalating energy level protocol or a fixed maximum energy protocol can be implemented. An escalating protocol may step the energy levels by using one or more techniques, such as linearly increasing the level with each successive shock (e.g., after an initial shock of 320 J, energy levels of 350 J and then 400 J may sequentially be used). Employing a fixed maximum energy level protocol, an energy level larger than the energy level used for the fixed lower energy level protocol can be implemented. After each shock, another AMSA transform value may be calculated from measurements to determine if the region of operation has changed. By using these regions defined by the AMSA transform value (e.g., 32 mV-Hz), an escalating energy protocol or a fixed maximum energy level protocol may improve defibrillation results when the AMSA transform values is relatively high (e.g., at or above 32 mV-Hz). When low (e.g., below 32 mV-Hz), an escalating energy protocol may not improve defibrillation results and a fixed low energy protocol may perform just as well as the escalating energy protocol. Through real-time AMSA analysis during a CPR, energy selection for defibrillation along with defibrillation timing can be optimized.

In some implementations, other therapeutic and/or shock delivery parameters can be adjusted based on the transform values. For example, the defibrillation shock may be delivered as a biphasic truncated exponential waveform. In this case, the overall duration of the waveform can be adjusted, e.g., within a range of 4 ms to around 22 ms. Alternatively or in addition, the duration of one or both phases can be adjusted (e.g., between 2 ms and 20 ms). Examples of other therapeutic and/or shock delivery parameters include, but are not limited to: peak defibrillation current, a minimum current to be delivered to the patient, energy values, first phase average defibrillation current or energy, defibrillation current or energy waveform duration, defibrillation peak voltage, defibrillation current or energy waveform rise or fall time, defibrillation current or energy tilt values, defibrillation average current or energy values, and defibrillation root mean square (RMS) current or energy values. Other defibrillation current, voltage, and/or energy parameters may be modified based on the transform values described herein. The therapeutic parameters may also include parameters that govern synchronized defibrillation. Synchronized defibrillation is also known as synchronized cardioversion. At low currents or energies, synchronized defibrillation may be beneficial for ECG waveforms with AMSA transform values higher than a threshold (e.g. AMSA transform values in excess of 38 to 40).

Figure 5:
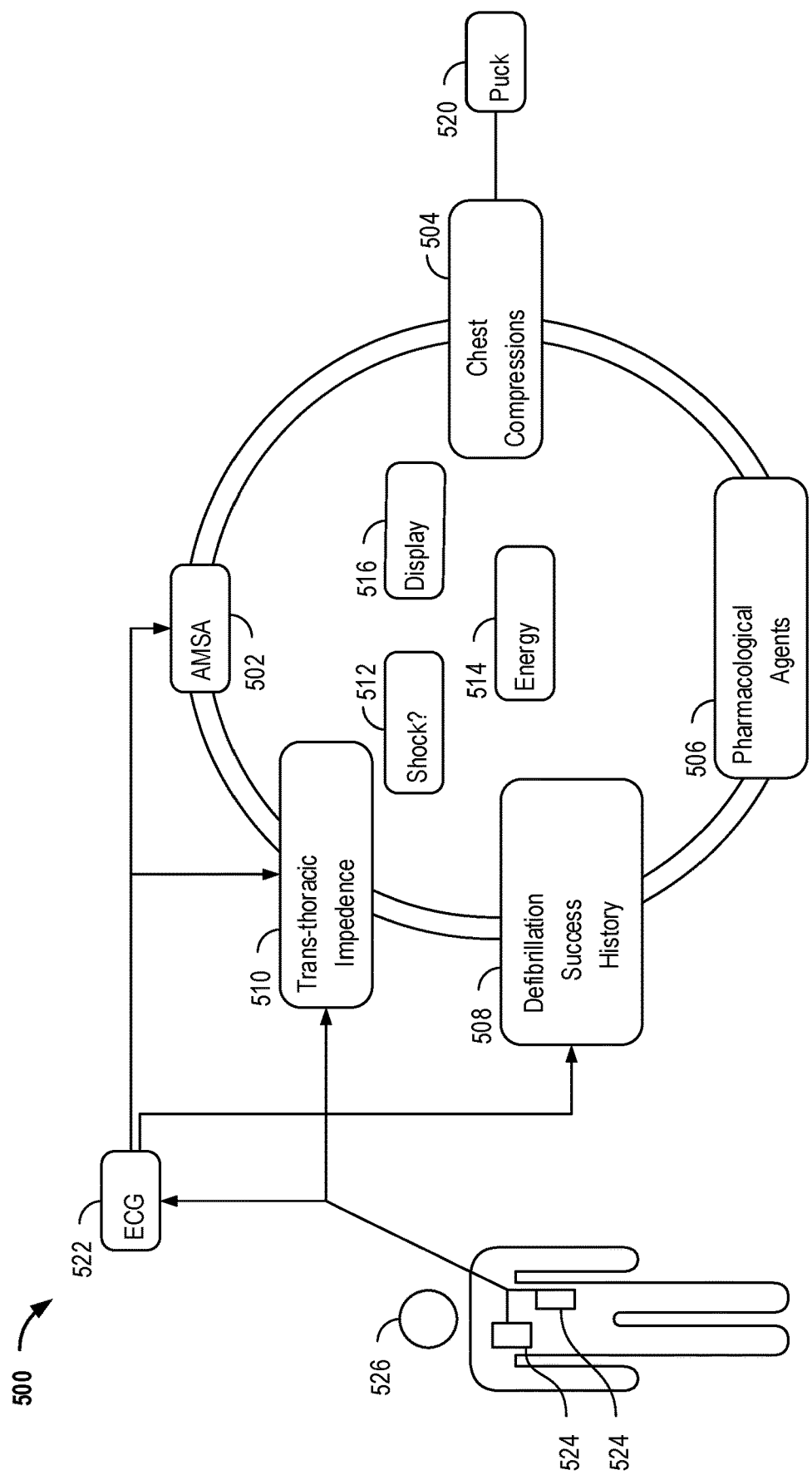
FIG. 5 shows consideration by a system of multiple signals in making shock determinations and recommendations.

FIG. 5 shows consideration by a system of multiple signals in making shock determinations and recommendations, as described with reference to FIGS. 9 and 10. As shown conceptually in FIG. 5, various input signals for determining a likelihood that a shock will be successful and for determining a best energy level for the shock are shown in a circle around the outputs that such signals may impact. In a particular implementation, one of the signals may be used alone, or multiple of the signals may be combined so as to create a composite energy or likelihood—e.g., by giving a score to each type and a weight, and combining them all to generate a weighted composite score for a likelihood.

The relevant signals may be generated from inputs that may obtain at least some of their data from signals generated by a pair of electrodes 524 that may be adhered to a patient's torso—above one breast and below the other, respectively, for example, in a typical manner. The electrodes may include leads for obtaining ECG data based on electrodes distributed within a garment worn about a torso of the patient and providing such data for analysis for a number of purposes. In addition, a CPR puck 520 may be placed on a patient's sternum and may deliver signals indicative of acceleration of the puck, and thus of up-down acceleration of the patient's sternum, which may be mathematically integrated so as to identify a depth of compression (and presence or absence of complete release) by the rescuer (and can also be used more simply to identify whether the patient is currently receiving chest compressions or not).

The electrodes 524 may be electrically connected to an ECG unit 522, which may be part of a wearable defibrillator and may combine data from different leads (e.g., 8 or 32 leads) in a familiar manner to construct a signal that is representative of the patient's 526 ECG pattern. The ECG combination may also be represented mathematically as a vector value, such as including vector components in an XYZ representation. Such an ECG signal is often used to generate a visual representation of the patient's 526 ECG pattern on a screen of the defibrillator. The ECG-related data may also be analyzed in various ways to learn about the current condition of the patient 526, including in determining what sort of shock indication to provide in order to control the defibrillator or to display to a rescuer.

As one such example, ECG data may be provided to a transform value (e.g., AMSA) analyzer 502, which may nearly continuously and repeatedly compute a transform value or a similar indicator that represents ECG amplitude at particular different frequencies and/or frequency ranges in an aggregated form (e.g., a numeral that represents a value of the amplitude across the frequencies). The transform value may be determined from vectorized versions of the ECG readings so as to provide more predictive transform values, as described with reference to FIGS. 1B and 1C. Similarly, power spectrum area can be measured and its value can be used as an input that is alternative to, or in addition to, the transform value for purposes of making a shock indication.

As described in more detail above and below, a current transform value (or a combination of multiple values over a short period taken in different windows of time) can be used to determine whether a shock is likely to be successful, and a plurality of combined transform values, such as a running average computed many times over a time period using a moving window may indicate how much time has elapsed since a cardiac event began and thus indicate which phase, of multiple phases during a VF event, the victim is in, where each phase calls for a different most-effective treatment sub-protocol. Also, when rescuers first arrive on a scene, several seconds of ECG data may be used to provide them an initial indication of the time since the event started and/or the phase in which the victim currently is in—e.g., by displaying a number of elapsed minutes or the name of one of multiple phases (like the three phases discussed above) on a display screen of a medical device such as a monitor or defibrillator/monitor.

The transform value analyzer 502 may be programmed to perform the analysis on the ECG inputs, and perhaps other inputs, so as to maximize the predictive value of the transform value readings, whether by affecting inputs to the transform value determination, and/or making the transform value determination and then adjusting the transform value that is generated from that determination. As one example, the size of the window in time from which ECG data is taken in making the calculation may be set to maximize the predictive value, such as by being about 3 second to about 3.5 seconds long. As another example, the shape of the window may be tapered, such as by being in the form of a Tukey or Hann window, rather than having vertical edges like a boxcar window. Similarly, the coefficients for the window, such as Chi2 and p may be set to maximize the expected predictive value of the calculation.

The transform value analyzer 502 may also be programmed to change such parameter values dynamically over the course of a particular VF incident, either by moving the values progressively as time elapses so as to make the values match known expected values for maximizing the predictive effect of the calculation, or to respond to particular readings, e.g., to use particular window length, form, or coefficients when an transform value is in a particular defined range.

The predictive quality of the transform value determination may also be increased by performing the FFT or other transform in making the calculation on a vector value rather than a scalar value from the leads. Such an approach may provide a more complete picture of the operation of the heart, such as by catching minimums and maximums in the various signals more reliably and in capturing a picture of a greater portion of the heart rather than a particular point on the heart, where such point might be less representative of the overall condition of the heart. The overall process may thus better represent the actual condition of the heart, rather the non-indicative random changes in the signals.

A CPR chest compression module 504 provides another signal and may receive signals about the motion of the puck 520 to determine whether chest compressions are currently being applied to the patient, and to determine the depth of such compressions and whether full release is occurring. Such information may be used, for example, in giving a rescuer feedback about the pace and depth of the chest compressions (e.g., the defibrillator could generate a voice that says "push harder"). The presence of current chest compression activity may also signal the other components that a shock is not currently advisable, or that ECG data should be analyzed in a particular manner so as to remove residual artifacts in the ECG signal from the activity of the chest compressions.

Information about pharmacological agents 506 provided to a patient may also be identified and taken into account as another signal in providing a shock indication to a rescuer and adjusting an energy level for any shock. Such information may be obtained manually, such as by a rescuer entering, via a screen on a defibrillator or on a tablet computer that communicates with the defibrillator, identifiers for the type of agent administered to a patient, the time of administration, and the amount administered. The information may also be obtained automatically, such as from instruments used to administer the particular pharmacological agents. The device that provides a shock indication may also take that information into account as yet another signal in identifying the likelihood that a shock will be successful if provided to the patient (e.g., by shifting up or down an transform value threshold for measuring shock success likelihood), and for other relevant purposes such as determining an energy to apply in the shock.

A defibrillation history success module 508 tracks the application of defibrillating shocks to the patient and whether they were successful in defibrillating the patient, and/or the level to which they were successful. For example, the module 508 may monitor the ECG waveform in time windows of various sizes for a rhythm that matches a profile of a "normal" heart rhythm, and if the normal rhythm is determined to be established for a predetermined time period after the application of a defibrillating shock, the module 508 may register the existence of a successful defibrillating shock. If a shock is applied and a normal rhythm is not established within a time window after the delivery of the shock, the module 508 can register a failed shock. In addition to registering a binary value of success/fail, the module may further analyze the ECG signal to determine the level of the success or failure and may, for example, assign a score to the chance of success of each shock, such as a normalized score between 0 (no chance of success) and 3 (absolute certainty).

With respect to modifying an transform value or other shock prediction algorithm (SPA) score, or affecting the manner in which such score is computed based on prior success or failure in delivering defibrillating shocks, it has been observed that victims of cardiac fibrillation will successfully defibrillate for lower transform value (e.g., below a threshold) if they have been previously successfully defibrillated during the same rescue session. Such a determination may also be combined with determinations about trans-thoracic impedance (trans-thoracic impedance) of the patient, or other measured factors, as discussed more fully below.

Particular techniques discussed here, including selection of proper window size for the ECG data, proper window type, proper coefficients, and the use of vectorized operations in calculating the transform value, may improve the quality of the transform value scoring process. A score based on the transform values may also be used to determine where, time-wise, a person is in the process of suffering from cardiac arrest and fibrillation, since defibrillating shocks may be much less effective after a person has been fibrillating for several minutes, and CPR (including forceful CPR) may be a preferred mode of treatment instead. Such systems may also combine a current transform value (e.g., for recommending a shock) with a trend in transform value over time (e.g., for recommending chest compressions instead of a shock), where some or all of the transform values may be made from vector input.

A trans-thoracic impedance module 510 may also obtain information from sensors provided with the electrodes 524, which indicates the impedance of the patient between the locations of the two electrodes. The impedance can also be a factor in determining a shock indication, such as by taking into account an impedance in altering the transform value score that will trigger a recommendation for providing a defibrillating shock. It would be understood that mathematically, such additional factors such as TTI may be used as inputs to a transform value-related calculation, or may be used to modify a result of transform value-related calculation.

One or more of the particular factors or signals discussed here may then be fed to a shock indication module 512 and/or an energy selection module 514, which may combine them each according to an appropriate formula so as to generate a binary or analog shock indication and a proposed energy level for a shock, respectively. For example, any of the following appropriate steps may be taken: a score may be generated for each of the factors, the scores may normalized (e.g., to a 0 to 3 or 0 to 500 scale), a weighting may be applied to each of the scores to represent a determined relevance of that factor to the predictability of a shock outcome or energy level to be delivered, the scores may be totaled or otherwise combined, and an indication can be determined such as a go/no go indication, a percentage of likely success, and other such indications.

The results of such determinations may also be provided to a display module 516, which may generate a presentation to be provided to a rescuer who is operating the defibrillator. Such presentation, may be visual, auditory, haptic, or a combination of the three. For example, if a shock is determined to be likely to succeed if it is provided, the display module 516 may cause a screen on the defibrillator to display a binary indication such as "Ready to deliver shock" or an analog indication such as "80% likelihood of successful shock." Similarly, the display module may cause a screen to show a message such as "200J." One or more of the messages may alternatively or additionally be spoken by computer-generated voice into a speaker on the defibrillator or into a wireless earpiece worn by a rescuer or rescuers.

In this manner then, the system 500 may take into account one or a plurality of factors and treat them as input signals in determining whether a shock to be delivered to a patient is likely to be successful. The factors may take data measured from a plurality of different inputs (e.g., ECG, TTI, delivered agents, etc.), and may be combined to create a likelihood indication, such as a numerical score that is to be measured against a predetermined scale (e.g., 0 to 500% likelihood or A to F grade). They may also be used to select an appropriate energy level for delivery of a shock. In some implementations, different ones of the factors may be used in the likelihood of success determination than in the energy level determination. Additional determinations may also be made with one or more of the signals. Such determinations may then be used to control an automatically-operated system (e.g., that delivers chest compressions mechanically), to limit operation of a manually-operated system (e.g., by enabling a shock that is triggered by a user pressing a button), or by simply providing information to a system whose shock is determined solely by a rescuer (e.g., for manual defibrillators in which the operator is a well-trained professional, or a hybrid defibrillator that is set in a manual mode).

Figure 6:
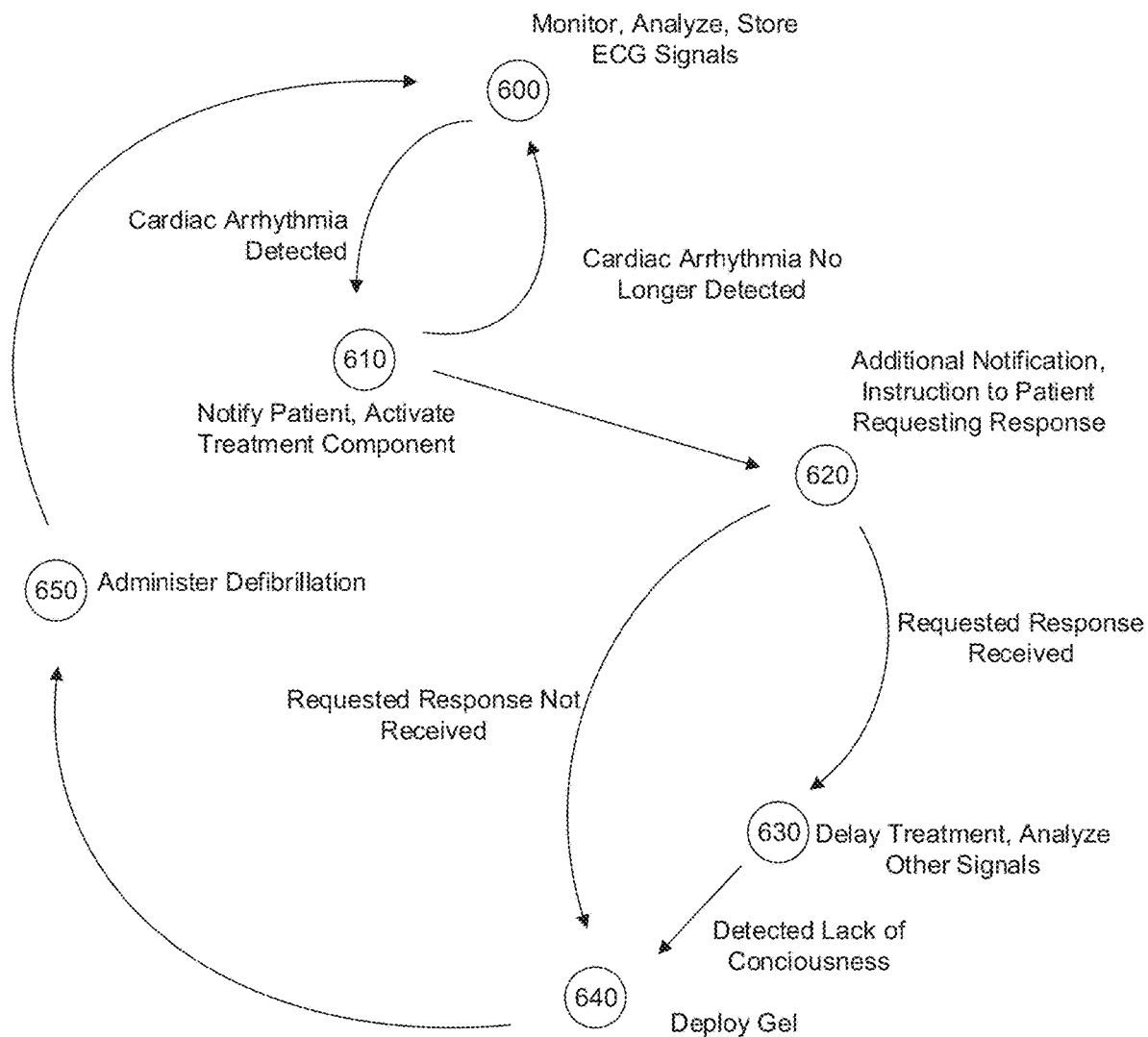
FIG. 6 is a state diagram showing various states of operation of a non-invasive, bodily attached ambulatory medical monitoring and treatment device.

FIG. 6 is a state diagram showing the various states of operation of a non-invasive bodily-attached ambulatory medical monitoring and treatment device, such as by currently available models of the LifeVest® Wearable Cardioverter Defibrillator. In state 600, which is the normal operating state of the device, the portable treatment controller monitors, analyzes, and records ECG signals obtained from the body of the patient. The analysis that is performed in state 600 generally includes QRS signal detection based upon digitized ECG signals, analyzing the morphology of the detected QRS signals and the patient's heart rate, axis analysis of patient's heart using vector cardiographic techniques, and the spectral analysis of various frequency components of patient's ECG signals, such as described in the '669 patent. In response to detecting a cardiac arrhythmia in state 600, the operation of the medical monitoring and treatment device proceeds to state 610.

In state 610, the portable treatment controller notifies the patient, and any bystanders that may be in the immediate vicinity of the patient, that it has detected a cardiac arrhythmia. The notification can include an audible alarm such as a siren, a verbal notification such as a reproduced voice command (for example, identifying that a cardiac arrhythmia has been detected), a printed message displayed on a visual display screen of the portable treatment controller, the associated watch or computer-enabled glasses, a tactile notification such as vibrations produced by a motor with an unbalanced weight on its shaft, or all of the above. In state 610, the portable treatment controller also activates a treatment component in preparation for providing one or more defibrillating shocks to the body of the patient. Activation of the treatment component generally includes the charging of one or more capacitors from a power supply of the medical monitoring and treatment device up to a level sufficient to provide one or more defibrillating shocks to the body of the patient via the therapy delivery interface 202 and the therapy electrodes 114. In state 610, the portable treatment controller typically issues another notification to the patient and any proximate bystanders, and continues to monitor the ECG signals obtained from the patient. The notification is similar to the notification provided in state 610. After activation of the treatment component, and the issuance of one or more alerts, the portable treatment controller proceeds to state 620. In response to determining in state 610 that the cardiac arrhythmia is no longer present, the portable treatment controller returns to state 600.

In state 620 the portable treatment controller continues to monitor the ECG signals obtained from the patient. In state 620, the one or more capacitors are fully charged and capable of delivering one or more defibrillating shocks to the body of the patient. In state 620, the portable treatment controller issues another notification to the patient and any proximate bystanders. The notification may be similar to the notification provided in state 610, but is followed by instructions to the patient and any bystanders that may be present. The instructions can include, for example, audible instructions that are communicated to the patient and any bystanders via a speaker on the portable treatment controller 120, the user interface pod, or the associated watch 145. The instructions can also include textual messages displayed on a visual display screen of the portable treatment controller, the associated watch, or computer-enabled glasses. The instructions can be configured, for example, to request the patient to provide a particular response, such as to press and hold one or more response buttons on the user interface pod, the portable treatment controller 120, or the associated watch 145, to indicate whether they are conscious. The instructions can also be configured to alert any bystanders not to provide the response and to move away from the patient because defibrillation is imminent. In response to providing the requested response, the portable treatment controller continues to monitor the ECG signals obtained from the patient and proceeds to state 630. In the event that the requested response is not provided, the portable treatment controller proceeds to state 640.

In state 630 the portable treatment controller sets a timer that delays the administration of defibrillation to the patient for a predetermined time, based on the receipt of the requested response. In some embodiments, the predetermined time is approximately 10 seconds. In state 630 the portable monitoring and treatment controller continues to monitor the ECG signals obtained from the patient and in some implementations monitors and analyzes other signals indicative of whether it was the patient, or another that provided the requested response. Such other signals may include signals obtained from one or more accelerometers on the wearable monitoring and treatment device indicative of the motion (e.g. consciousness) of the patient or the inactivity (e.g., lack of consciousness) of the patient, signals received from the body of the patient during actuation of the one or more response buttons (and which uniquely identify the patient as having provided the requested response), etc. In response to determining that the other signals were provided by someone other than the patient, or the other signals, such as patient activity signals obtained from one or more of the accelerometers indicate that the patient is not conscious, the portable treatment controller proceeds to state 640.

In state 640 the portable treatment controller continues to monitor the ECG signals obtained from the body of the patient, activates an impedance reducing gel-dispensing mechanism that is operatively coupled to the therapy electrodes, and proceeds to state 650. In state 650 the portable treatment controller administers a defibrillating shock to the body of the patient. After administration of the defibrillating shock in state 650, the portable treatment controller returns to state 600.

Figure 7:
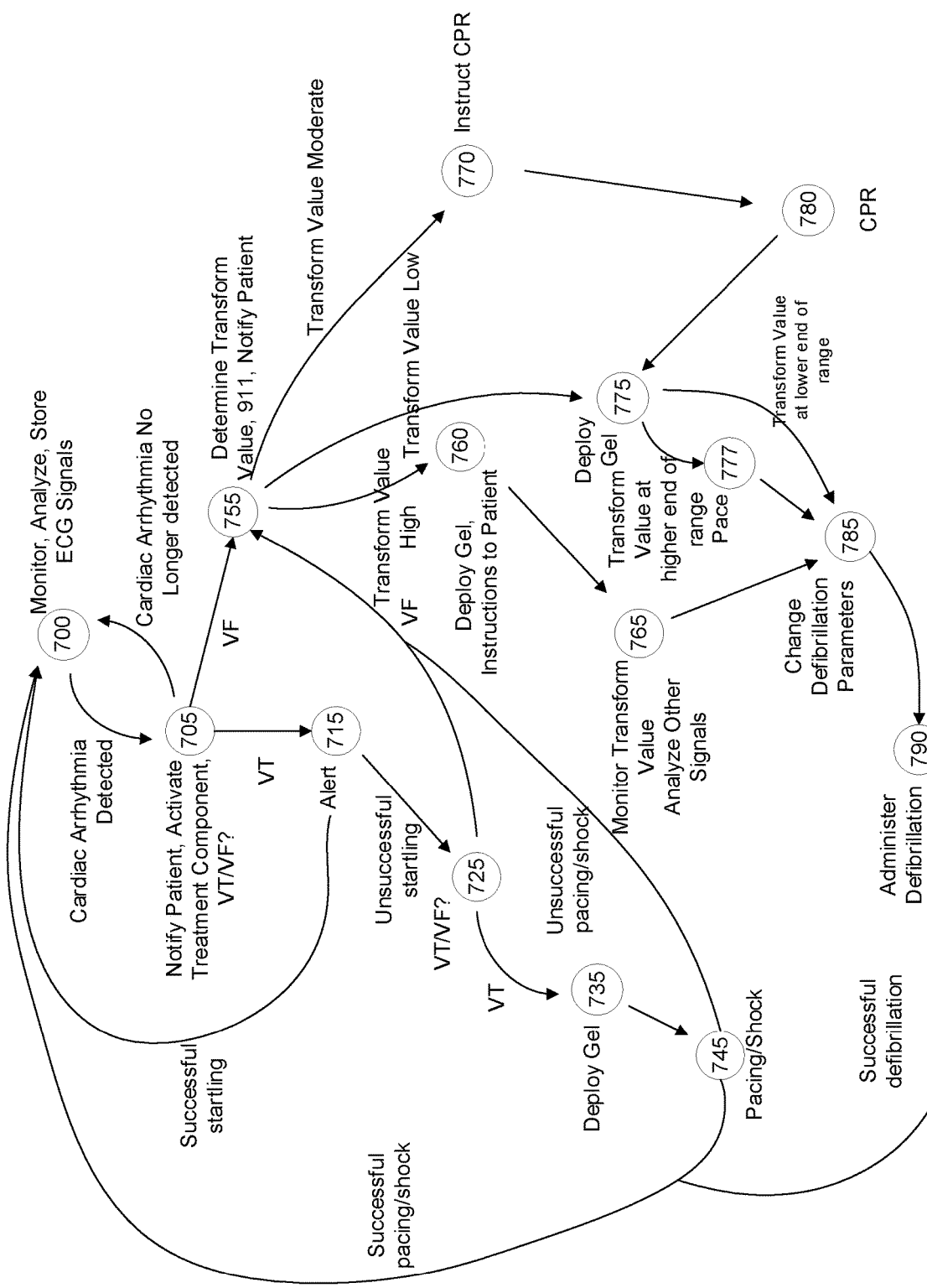
FIG. 7 is a state diagram showing various states of operation of a non-invasive, bodily attached ambulatory medical monitoring and treatment device.

FIG. 7 is a state diagram showing the various states of operation of a non-invasive ambulatory monitoring and treatment device in accordance with an embodiment of the present technology. In contrast to the operation described with respect to FIG. 3, various states of operation of the monitoring and treatment device of the embodiment also consider additional information, such as transform values (e.g., AMSA) of the VF rhythm to determine whether to initiate, hasten or delay the application of a defibrillating shock to the patient. For example, the AMSA transform score can be used along with other processes described below to classify between a noise rhythm and a shockable cardiac arrhythmia rhythm, e.g., a shockable VT/VF rhythm. If it is determined that the patient is suffering a life-threatening condition such as a shockable VT rhythm or a shockable VF rhythm, the device can initiate the treatment alarm sequence, which in some instances, culminates in the application of the defibrillating shock within minutes, e.g., between 25 seconds and 180 seconds. For example, if the arrhythmia event is a shockable VT event, a default response time may be 60 seconds, and can be configured to be adjusted within a range of 60 to 180 seconds. For example, if the arrhythmia event is a shockable VF event, a default response time may be 25 seconds, and can be configured to be adjusted within a range of 25 to 60 seconds. If a treatment alarm sequence is ongoing, in some examples, based on the transform score and other inputs the device can hasten the application of the defibrillation shock so that the shock is delivered sooner than the default of configured time. Otherwise, the device can delay the shock, for example, an additional 25-45 seconds, as described in further detail below in connection with FIGS. 9 and 10. In state 700, which is the normal operating state of the device, the portable treatment controller monitors, analyzes, and records ECG signals obtained from the body of the patient. The analysis that is performed in state 700 generally includes QRS signal detection based upon digitized ECG signals, analyzing the morphology of the detected QRS signals and the patient's heart rate, axis analysis of patient's heart using vector cardiographic techniques, and the spectral analysis of various frequency components of patient's ECG signals, such as described in the '669 patent, and as described above with respect to FIG. 3. In response to detecting a cardiac arrhythmia in state 700, the operation of the medical monitoring and treatment device proceeds to state 705.

In state 705, the portable treatment controller notifies the patient, and any bystanders that may be in the immediate vicinity of the patient, that it has detected a cardiac arrhythmia. The notification can include the notifications previously described with respect to state 310, such as an audible alarm, a verbal notification, a textual message (e.g., displayed on a visual display screen of the portable treatment controller, the associated watch, or computer-enabled glasses), a tactile notification, or a combination of the above. In state 705, the portable treatment controller also activates a treatment component in preparation for providing one or more defibrillating shocks to the body of the patient. As previously described, activation of the treatment component generally includes the charging of one or more capacitors from a power supply of the medical monitoring and treatment device up to a level sufficient to provide one or more defibrillating shocks to the body of the patient via the therapy delivery interface 202 and the therapy electrodes 114. In state 705, the portable treatment controller continues to monitor the ECG signals obtained from the patient, but also makes a determination as to whether the detected cardiac arrhythmia corresponds to a treatable type of VT, or to VF. In response to determining that the detected cardiac arrhythmia corresponds to a treatable type of VT, the portable treatment controller proceeds to state 715, and in response to determining that the detected type of cardiac arrhythmia corresponds to VF, the portable treatment controller proceeds to state 755. In response to determining in state 705 that the cardiac arrhythmia is no longer present, the portable treatment controller returns to state 700 to continue to monitor, analyze and/or store ECG signals of the patient.

In state 715 the one or more capacitors are fully charged and capable of delivering one or more defibrillating shocks to the body of the patient, and the portable treatment controller continues to monitor the ECG signals obtained from the patient. In state 715, in response to determining that the detected cardiac arrhythmia corresponds to a treatable type of VT, the portable treatment controller issues another notification (i.e., a high intensity alert) to the patient and any proximate bystanders. The notification may be similar to the notification provided in state 705, but is provided at a significantly increased intensity (e.g., volume level and/or vibration level), in an attempt to terminate VT and return the patient's heart to a sinus rhythm. In response to determining that VT treatment was successful, the portable treatment controller returns to state 700. Alternatively, in response to determining that VT treatment did not return the patient to a viable perfusing cardiac rhythm, the portable treatment controller proceeds to state 725.

In state 725, the portable treatment controller continues to monitor the ECG signals obtained from the patient and again makes a determination as to whether the detected cardiac arrhythmia corresponds to a treatable type of VT or VF (e.g., a shockable VT or VF rhythm). In response to determining that the detected cardiac arrhythmia corresponds to a treatable type of VT, the portable treatment controller proceeds to state 735. Alternatively, in response to determining that the detected cardiac arrhythmia has degraded from VT to VF the portable treatment controller proceeds to state 755.

In state 735, in response to determining that the detected cardiac arrhythmia corresponds to a treatable form of VT, the portable treatment controller continues to monitor the ECG signals obtained from the body of the patient. The portable treatment controller also activates an impedance reducing gel-dispensing mechanism that is operatively coupled to the therapy electrodes in preparation for the administration of a low-level electrical shock configured to terminate VT, or the administration of external pacing configured to prevent the onset of VF. After activation of the impedance reducing gel, the portable treatment controller proceeds to state 745.

In state 745, the portable treatment controller continues to monitor the ECG signals obtained from the patient and based on that monitoring, makes a determination as to whether to administer a relatively low-level shock (e.g., 1 mA to 20 mA) to the body of the patient in an attempt to treat VT and to return the patient to a perfusing rhythm, to apply pacing to the body of the patient in an attempt to gain control of the patient's heart, or both. The pacing that may be applied to the heart of the patient in state 745 may include pacing the heart of a patient at a fixed rate and fixed energy, or pacing the heart of the patient using an adjustable rate and/or energy level (e.g., capture management pacing), such as overdrive pacing. In overdrive pacing, a series of pacing pulses (e.g., between about 5 and 10 pacing pulses) are delivered to the patient at a frequency above the detected intrinsic heart rate of the patient in an effort to gain control of the patient's heart rate, and which once in control of the patient's heart rate, the rate (i.e., the frequency) of the pulses are decremented until the detected intrinsic cardiac rate of the patient is at or below a typical heart rate of the patient. In response to determining that the low-level shock and/or pacing administered in state 745 is effective at returning the patient's heart to a perfusing rhythm, the portable treatment controller returns to state 700. Alternatively, in response to determining that the low-level shock and or pacing is not successful, and the patient degrades to VF, the portable treatment controller proceeds to state 755 to determine a transform value and further to alert an emergency responder as well as notify the patient.

In response to determining in any of states 705, 725, or 745 that the detected cardiac arrhythmia corresponds to a shockable VF rhythm, the portable treatment controller proceeds to state 755. In state 755, the one or more capacitors are fully charged and capable of delivering one or more defibrillating shocks to the body of the patient and the portable treatment controller continues to monitor the ECG signals obtained from the body of the patient. The portable treatment controller sends a communication (e.g., cellular or wireless) via the communication network interface 206 (FIG. 2) to alert an emergency responder as to the status and location of the patient. In state 755, the portable treatment controller additionally determines transform values indicative of the metabolic state of patient's heart. As described previously, the determination of transform values may be based on time domain samples of the patient's ECG signals that are transformed to the frequency domain, for example, using an FFT transform, by a processor of the portable treatment controller, such as a DSP processor. In accordance with an aspect of the present technology, the transform values may be determined over a time window of approximately one to six seconds. Dependent upon the transform values determined by the portable treatment controller in state 755, and how the transform values change over time, the operation of the portable treatment controller may vary. For example, in response to determining that the patient's transform values are relatively high (about 21 mV*Hz or more) and reflect high metabolic state of the heart of the patient and a high probability of successful defibrillation, the portable treatment controller proceeds to state 760. In response to determining that the patient's AMSA values are low (below about 10 mV*Hz or more) and reflect a low metabolic state of the heart of the patient and a low probability of successful defibrillation, the portable treatment controller proceeds to state 775. In response to determining that the patient's transform values are intermediate (between approximately 10 mV*Hz and 20 mV*Hz), the portable treatment controller proceeds to state 770 to monitor the ECG signals obtained from the body of the patient, determine updated transform values indicative of the metabolic state of patient's heart, and issue instructions to perform CPR on the patient in an effort to improve the metabolic state of the patient's heart so that defibrillation is more likely to be effective.

In state 760, the portable treatment controller continues to monitor the ECG signals obtained from the body of the patient and determines updated transform values indicative of the metabolic state of patient's heart. The portable treatment controller activates the impedance reducing gel dispensing mechanism that is operatively coupled to the therapy electrodes in preparation for the administration of a defibrillating shock (if it has not been previously activated in state 735), and issues instructions to the patient and any bystanders that may be present. The instructions can include, for example, audible instructions that are communicated to the patient and any bystanders via a speaker on the portable treatment controller 120, the user interface pod, and/or the associated watch 145. The instructions can also include textual messages displayed on a visual display screen of the portable treatment controller, the associated watch, or computer-enabled glasses. The instructions can be configured, for example, to request the patient to provide a particular response, such as to press and hold one or more response buttons on the user interface pod, the portable treatment controller 120, or the associated watch 145, to indicate whether they are conscious. The instructions can also be configured to alert any bystanders not to provide the response and to move away from the patient because defibrillation is imminent. The portable treatment controller sets a timer (e.g., 10 seconds) to await a response from the patient, and proceeds to state 765.

In state 765, the portable treatment controller continues to monitor the ECG signals obtained from the patient and determines updated transform values. In response to determining that the updated transform values have not changed (i.e., declined) appreciably from those determined in states 755 and 760, the portable treatment controller may await the requested response from the patient, analyze other signals that may be indicative of the consciousness or lack of consciousness of the patient and expiration of the timer before proceeding to state 785. Alternatively, if the transform values determined in state 765 have decreased appreciably (e.g., by about 10% or more) from those determined in state 760, the requested response has not been received by the patient, and other signals (such as information from one or more accelerometers) are indicative of a lack of consciousness, or signals from other sensors such as EMG sensors indicate the presence of a seizure (often a precursor to a lack of consciousness), the portable treatment controller proceeds immediately to state 785 to change defibrillation parameters and, subsequently, to 790 to administration defibrillation shocks without waiting for an expiration of the timer.

In state 785, the transform value is used to modify one or more therapeutic and/or shock delivery shock parameters. Examples of such therapeutic and/or shock delivery parameters include, but are not limited to: peak defibrillation current or energy values, peak-to-peak defibrillation current or energy values first phase average defibrillation current or energy, defibrillation current or energy waveform duration, defibrillation peak voltage, defibrillation current or energy waveform rise or fall-time, defibrillation current or energy tilt values, defibrillation average current or energy values, and defibrillation root mean square (RMS) current or energy values. Other defibrillation current, voltage, and/or energy parameters may be modified based on the transform values described herein.

In state 790, the portable treatment controller administers a defibrillating shock to the body of the patient. After administration of the defibrillating shock in state 790, the portable treatment controller may return to state 700 if it is determined that the defibrillation was successful. However, dependent on transform values, the portable treatment controller may instead deliver another defibrillating shock. For example, if transform values were at a relatively high level prior to defibrillation, and the defibrillation shock does not appear to have been effective, the portable treatment controller may deliver another defibrillating shock within as little as 10 seconds or less after the initial defibrillating shock. The is because although it may take as much as 40-45 second to determine whether a defibrillating shock was successful, it takes significantly less time to determine whether a defibrillating shock was not successful.

In response to determining in state 755 that the patient's transform values are low (below about 10 mV*Hz or more), the portable treatment controller proceeds to state 775, wherein the portable treatment controller activates the impedance reducing gel dispensing mechanism (if it has not been previously activated in state 735) that is operatively coupled to the therapy electrodes in preparation for the administration of a defibrillating shock. Because the determined low transform values reflect a relatively low probability of survival and a defibrillation shock may be the patient's best chance at survival, the portable treatment controller then proceeds immediately to state 785 and, subsequently, to 790 in an attempt to save the life of the patient, wherein the portable treatment controller administers a defibrillating shock to the body of the patient. In the event that the defibrillating shock is not successful, the portable treatment controller proceeds to state 770.

In some embodiments, the portable treatment controller need not proceed immediately to state 785 after deploying the impedance reducing gel in state 775. For example, in response to determining that the patient's transform values are low, but near the higher end of the scale (e.g., between 8-10 mV*Hz or so), the portable treatment controller may optionally proceed to state 777. In state 777, the portable treatment controller may continue to monitor the ECG signals obtained from the patient and apply pacing to the body of the patient in an attempt to gain control of the patient's heart. The pacing that may be applied to the heart of the patient in state 777 may include pacing the heart of a patient at a fixed rate and fixed energy, or pacing the heart of the patient using an adjustable rate and/or energy level (e.g., capture management pacing), such as described previously. In response to determining that the pacing was not successful, the portable treatment controller proceeds to state 785 to change defibrillation parameters and, subsequently, to 790 to administer defibrillation shocks.

Alternatively, in response to determining in state 755 that the patient's transform values are intermediate (between approximately 10 mV*Hz and 20 mV*Hz), but not indicative of a high probability of success, the portable treatment controller proceeds to state 770. In state 770, the portable treatment controller continues to monitor the ECG signals obtained from the body of the patient and determines updated transform values indicative of the metabolic state of patient's heart. The portable treatment controller also issues instructions, such as by a textual message on a visual display screen of the portable treatment controller or the associated watch, and audible instructions to any proximate bystanders, to perform CPR on the patient in an effort to improve the metabolic state of the patient's heart so that defibrillation is more likely to be effective. After issuing the instructions to perform CPR on the patient, the portable treatment controller proceeds to state 780.

In state 780, the portable treatment controller continues to monitor the ECG signals obtained from the body of the patient and determines updated transform values indicative of the metabolic state of patient's heart. The portable treatment controller also monitors signals, such as those provided by the one or more accelerometers provided on the wearable treatment device, to determine whether CPR is being administered to the patient. In the event that the portable treatment controller determines that CPR is being administered to the patient, the portable treatment controller may continue to monitor the ECG signals and continue to determine transform values to detect whether the administration of CPR is having a beneficial effect. In the event that the CPR is having a beneficial effect, the portable treatment controller may continue to monitor the ECG signals and determine updated transform values until the probability of successful defibrillation (as indicated by the updated transform values) increases to a point where defibrillation is likely to be successful. In response to determining that defibrillation has a sufficiently high probability of success, the portable treatment controller may instruct the bystander to discontinue CPR and move away from the patient, so that the impedance reducing gel may be deployed in state 775 and a defibrillation shock administered in state 785. Alternatively, in response to determining by the portable treatment controller that CPR is not being administered to the patient, the portable treatment controller may proceed immediately to states 775 to deploy gel, 785 to change defibrillation parameters, and 790 to administer defibrillator shocks.

Although the ability to use additional metrics of the metabolic state of a patient's heart, such as transform values, to vary the type of therapy, and the timing of that therapy is particularly well suited to a non-invasive, ambulatory medical monitoring and treatment device, such as the LifeVest® cardioverter defibrillator, such functionality could also be implemented in an Automated External Defibrillator (AED) or an Advanced Life Support (ALS) type of defibrillator, such as the M Series defibrillator, R Series ALS defibrillator, R Series Plus defibrillator, or E Series defibrillator manufactured by the ZOLL Medical Corporation of Chelmsford Mass.

In the above-described embodiments, transform values are determined over a window of time of approximately one to six seconds. The determined transform values are generally indicative of the metabolic state of the patient's heart, with higher transform values reflecting a better metabolic state. However, in other embodiments, transform values may be determined over a shorter period of time, such as a window of time of two seconds, or even one second. Such windows of time may be successive windows of time that do not overlap with one another, or they may be overlapping windows of time in which one window overlaps in time with a successive window by, for example, approximately 200 milliseconds. Even if transform values determined over such shorter windows of time are not adequately indicative of the metabolic state of a patient's heart, they can be used in predicting whether an intervention, such as defibrillation, might be successful at restoring a perfusing cardiac rhythm. In particular, transform values determined over a shorter window of time can be used to determine when to apply the intervention to the body of the patient to increase the probability of restoring a perfusing cardiac rhythm.

In a second set of experiments, ECG data from the above experiments was again analyzed using a variety of different ECG analysis techniques. A spectral analysis of the VF rhythms obtained from the ECGs of the approximately fifteen patients that initially exhibited VT and which then degraded into VF was again performed, and transform values were determined. However, the transform values determined in the second set of experiments were determined over progressively shorter windows of time. In the second set of experiments, as the window of time over which the transform values were determined became progressively shorter, the variation in transform value from one window to the next became more pronounced. Based on the second set of experiments, Applicants identified that during early stages of VF, transform values determined over a window of time of approximately one second changed significantly from one window to the next. When the transform values obtained over successive windows of time were analyzed over a period of time of about six seconds or more, the variation in transform values exhibited a generally sinusoidal shape, increasing and then decreasing in value in a periodic manner. In analyzing the transform values of those patients in which defibrillation was successful relative to those in which defibrillation was not successful, Applicants determined that defibrillation was successful at restoring a perfusing cardiac rhythm when the defibrillation was applied at a time corresponding to locally maximum transform values, as opposed to other times, and in particular, as opposed to times corresponding to locally minimum transform values.

In accordance with a further aspect of the present technology, transform values determined over various length windows of time may be used to determine whether the application of electrical therapy, such as defibrillation, can be expedited or delayed. In response to determining that electrical therapy can be applied, it is determined when such electrical therapy can be applied to the patient to increase the probability of a successful intervention. For example, transform values determined over a window of approximately one to four seconds may be used to determine whether to expedite or delay the application of electrical therapy. Transform values determined over a smaller window of approximately one second may be used to identify when to apply that electrical therapy to increase the probability of successful intervention.

Figure 8:
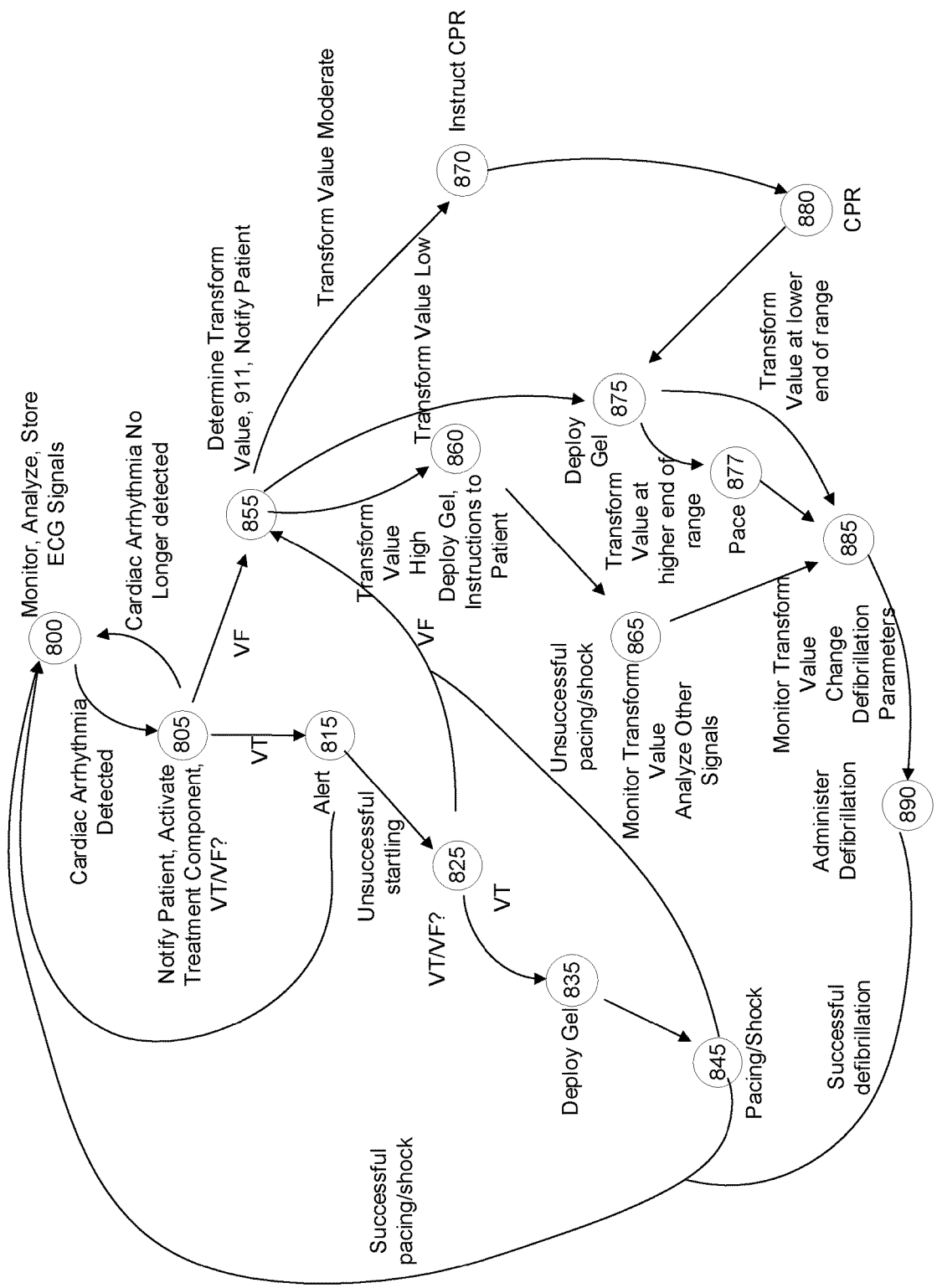
FIG. 8 is a state diagram showing various states of operation of a non-invasive, bodily attached ambulatory medical monitoring and treatment device.

FIG. 8 is a state diagram showing the various states of operation of a non-invasive ambulatory monitoring and treatment device in accordance with another embodiment of the present technology. The various states shown in FIG. 8 generally correspond to similar states described above with respect to FIG. 4, and are designated by similar reference numerals (e.g., state 805 in FIG. 8 corresponds to state 405 in FIG. 4, state 855 in FIG. 8 corresponds to state 455 in FIG. 4, etc.) Accordingly, those states of operation that are similar to those described previously with respect to FIG. 4 are described only briefly herein.

As in the embodiment described with respect to FIG. 4, the various states of operation of the monitoring and treatment device of the embodiment also consider additional information, such as transform values (e.g., AMSA) of the VF rhythm to determine whether to in or delay the application of a defibrillating shock to the patient. As in the embodiment described with respect to FIG. 4, such transform values are determined over a relatively long window of time, such as two seconds, and are generally indicative of the metabolic state of the patient's myocardium. However, various states of operation of the embodiment further determine transform values over shorter windows of time, and use those transform values to identify when electrical therapy can be applied.

In state 800, which is the normal operating state of the device, the portable treatment controller monitors, analyzes, and records ECG signals obtained from the body of the patient. As noted previously, the analysis generally includes QRS signal detection based upon digitized ECG signals, analyzing the morphology of the detected QRS signals and the patient's heart rate, axis analysis of patient's heart, and the spectral analysis of various frequency components of patient's ECG signals. In response to determining that a cardiac arrhythmia is detected in state 800, the medical monitoring and treatment device proceeds to state 805 wherein the portable treatment controller notifies the patient, and any bystanders, that it has detected a cardiac arrhythmia. The notification can be audible, verbal, written (e.g., a textual message displayed on a visual display screen of the portable treatment controller, the associated watch or computer-enabled glasses), tactile, or all of the above.

In state 805, the portable treatment controller also activates a treatment component in preparation for providing one or more defibrillating shocks to the body of the patient. As previously described, the generally includes charging of one or more capacitors to a level sufficient to provide one or more defibrillating shocks to the body of the patient via the therapy delivery interface 202 and the therapy electrodes 114. In state 805, the portable treatment controller continues to monitor the ECG signals obtained from the patient, and also makes a determination as to whether the detected cardiac arrhythmia corresponds to a treatable type of VT, or to VF. In response to determining that the detected cardiac arrhythmia corresponds to a treatable type of VT, the portable treatment controller proceeds to state 815. In response to determining that the detected type of cardiac arrhythmia corresponds to VF, the portable treatment controller proceeds to state 855. In response to determining in state 805 that the cardiac arrhythmia is no longer present, the portable treatment controller returns to state 800.

In state 815 the portable treatment controller continues to monitor the ECG signals obtained from the patient, and in response to determining that the detected cardiac arrhythmia corresponds to a treatable type of VT, the portable treatment controller issues another notification to the patient and any proximate bystanders. As noted previously, the notification can be provided at a significantly increased intensity (e.g., volume level and/or vibration level), in an attempt to terminate VT. In response to determining that the notification is successful in returning the patient to perfusing cardiac rhythm, the portable treatment controller returns to state 800. Alternatively, in response to determining that the notification does not return the patient to a viable perfusing cardiac rhythm, the portable treatment controller proceeds to state 825.

In state 825, the portable treatment controller continues to monitor the ECG signals obtained from the patient and again makes a determination as to whether the detected cardiac arrhythmia corresponds to a treatable type of VT, or to VF. In response to determining that the detected cardiac arrhythmia still corresponds to a treatable type of VT, the portable treatment controller proceeds to state 835. Alternatively, in response to determining that the detected cardiac arrhythmia has degraded from VT to VF the portable treatment controller proceeds to state 855.

In state 835, in response to determining that the detected cardiac arrhythmia corresponds to a treatable form of VT, the portable treatment controller continues to monitor the ECG signals obtained from the body of the patient and activates the impedance reducing gel dispensing mechanism that is operatively coupled to the therapy electrodes in preparation for the administration of a low-level shock configured to terminate VT, or the administration of external pacing. The portable treatment controller then proceeds to state 845.

In state 845, the portable treatment controller continues to monitor the ECG signals obtained from the patient and based on that monitoring, makes a determination as to whether to administer a relatively low-level shock (e.g., 1 mA to 20 mA) to the body of the patient in an attempt to terminate VT and to return the patient to a perfusing rhythm, to apply pacing to the body of the patient in an attempt to gain control of the patient's heart, or both. As described previously, the pacing applied in state 445 may include pacing the heart of a patient at a fixed rate and fixed energy, or pacing the heart of the patient using an adjustable rate and/or energy level (e.g., capture management pacing), such as overdrive pacing. In response to determining that the low-level shock and/or pacing was effective at returning the patient's heart to a perfusing rhythm, the portable treatment controller returns to state 800. Alternatively, in response to determining that the low-level shock and or pacing was not successful, and the patient degrades to VF, the portable treatment controller proceeds to state 855.

In response to determining in any of states 805, 825, or 845 that the detected cardiac arrhythmia corresponds to VF, the portable treatment controller proceeds to state 855. In state 855, the portable treatment controller continues to monitor the ECG signals obtained from the body of the patient and sends a communication (e.g., cellular or wireless) via the communication network interface 206 (FIG. 2) to alert an emergency responder as to the status and location of the patient. The portable treatment controller additionally determines transform values indicative of the metabolic state of patient's heart. As described previously, the determination of transform values may be based on time domain samples of the patient's ECG signals obtained over a time window of approximately two seconds that are transformed to the frequency domain, for example, using an FFT transform, by a processor of the portable treatment controller, such as a DSP processor. Dependent upon the transform values determined by the portable treatment controller in state 855, and how the transform values change over time, the operation of the portable treatment controller may vary. For example, in response to determining that the patient's transform values are relatively high (about 21 mV*Hz or more), the portable treatment controller proceeds to state 860. Alternatively, in response to determining that the patient's transform values are low (below about 10 mV*Hz or more), the portable treatment controller proceeds to state 875. In response to determining that the patient's transform values are intermediate (between approximately 10 mV*Hz and 20 mV*Hz), the portable treatment controller proceeds to state 870.

In state 860, the portable treatment controller continues to monitor the ECG signals obtained from the body of the patient and determines updated transform values indicative of the metabolic state of patient's heart. The portable treatment controller activates the impedance reducing gel dispensing mechanism (if it has not been previously activated in state 835), and issues instructions to the patient and any bystanders that may be present. As previously described, the instructions can include, for example, audible instructions that are communicated to the patient and any bystanders via a speaker on the portable treatment controller 120, the user interface pod, or the associated watch 145. The instructions can also include textual messages displayed on a visual display of the portable treatment controller, the associated watch, or computer-enabled glasses. The instructions can be configured to request the patient to provide a particular response, such as to press and hold one or more response buttons on the user interface pod, or on the portable treatment controller 120 or the associated watch 145, to indicate whether they are conscious. The instructions can also be configured to alert any bystanders not to provide the response and to move away from the patient because defibrillation is imminent. The portable treatment controller sets a timer (e.g., 10 seconds) to await a response from the patient, and proceeds to state 865.

In state 865, the portable treatment controller continues to monitor the ECG signals obtained from the patient and determines updated transform values. In response to determining that the updated transform values have not changed (i.e., declined) appreciably from those determined in states 855 and 860, the portable treatment controller may await the requested response from the patient, analyze other signals that may be indicative of the consciousness or lack of consciousness of the patient and expiration of the timer before proceeding to state 885. Alternatively, if the transform values determined in state 865 have decreased appreciably (e.g., by about 10% or more) from those determined in state 860, the requested response has not been received by the patient, and other signals (such as information from one or more accelerometers) are indicative of a lack of consciousness, or signals from other sensors such as EMG sensors indicate the presence of a seizure (often a precursor to a lack of consciousness), the portable treatment controller proceeds immediately to state 885 and, subsequently, to 890 without waiting the expiration of the timer.

In state 885, the portable treatment controller continues to monitor the ECG signals obtained from the patient and determines transform values. However, in state 890, the transform values are determined over much smaller windows of time than those determined in states 855 and 865. In accordance with an aspect of the present technology, the transform values determined in state 890 are based on a window of time of approximately one second in duration, and transform values are successively determined for a period of time of approximately six to eight seconds. The windows of time over which the transform values are determined in state 890 may be successive windows of time that do not overlap with one another, or they may be overlapping windows of time in which one window overlaps in time with a successive window by, for example, approximately 200 milliseconds. In state 885, the portable treatment controller monitors the transform values determined over successive windows (of approximately one second in duration) to determine if and how to use the transform value to modify one or more therapeutic and/or shock delivery shock parameters. Examples of such therapeutic and/or shock delivery parameters include, but are not limited to: peak defibrillation current or energy values, peak-to-peak defibrillation current or energy values first phase average defibrillation current or energy, defibrillation current or energy waveform duration, defibrillation peak voltage, defibrillation current or energy waveform rise or fall-time, defibrillation current or energy tilt values, defibrillation average current or energy values, and defibrillation root mean square (RMS) current or energy values. Other defibrillation current, voltage, and/or energy parameters may be modified based on the transform values described herein. In state 890, a defibrillation shock is administered to the patient with adjusted defibrillation parameters.

As noted previously, during early stages of VF, transform values determined over a window of time of approximately one-second change from one window to the next in a periodic manner having a generally sinusoidal shape when viewed over a period of time of about six seconds or more. Accordingly, in state 885 the portable treatment controller monitors the transform values over successive windows to predict the point in time when the transform value is at a locally maximum value, to adjust defibrillation parameters, and, in state 890, to apply defibrillation to the patient at that point in time when the transform value is a local maximum. The prediction and the adjustment may be done in a number of different ways. For example, in one embodiment, the portable treatment controller determines a local minimum transform value over a period of about six to eight seconds, adjusts the defibrillation parameters, and then applies defibrillation when the transform values are trending upward, and have a value that satisfies a threshold condition (e.g., is 50% greater than the local minima). In another embodiment, the portable treatment controller can determine a local maximum transform value over the period of about six to eight seconds, adjusts the defibrillation parameters, and then applies defibrillation when the transform values are trending upward, and have a value that satisfies a threshold condition (e.g., is 75% of the local maxima). In yet another embodiment, the portable treatment controller can determine local maxima and minima transform values over the period of about six to eight seconds, adjusts the defibrillation parameters, and then applies defibrillation when the transform values are trending upward, and have a value that satisfies a threshold based on the determined transform values (e.g., is greater than the average of the local minima and the local maxima, is greater than a certain percentage of the local minima, the local maxima, or a combination of the local minima and the local maxima). In some implementations, a combination of the different approaches described above may be used to determine when the transform values are trending upward and approaching a local maximum, and to control the timing of the defibrillation to generally coincide with the local maximum to increase the probability of successful defibrillation. Embodiments of the present technology are not limited to any one specific approach.

In state 890, after determining when defibrillation can be applied to the body of the patient, the portable treatment controller applies defibrillation to the patient at the predicted time to increase the probability of successful defibrillation. After administration of the defibrillating shock in state 890, the portable treatment controller may return to state 800 if it is determined that the defibrillation was successful. In some implementations, the portable treatment controller may return to state 885, and, dependent on transform values, the portable treatment controller may instead readjust the defibrillation parameters and proceed to state 890 to deliver another defibrillating shock as described previously with respect to FIG. 7.

In response to determining in state 855 that the patient's transform values are low (below about 10 mV*Hz or more), the portable treatment controller proceeds to state 875, wherein the portable treatment controller activates the impedance reducing gel dispensing mechanism (if it has not been previously activated in state 835) in preparation for the administration of a defibrillating shock. The portable treatment controller then proceeds either directly to state 885, or to state 877. For example, in response to determining that the transform values are low, but near the higher end of the scale (e.g., between 8-10 mV*Hz or so), the portable treatment controller may proceed to state 877, wherein pacing may be applied in the manner previously described. In response to determining that the pacing performed in state 877 was not effective, the portable treatment controller may then proceed to states 885 and 890. Alternatively, in response to determining in state 855 that the transform values of the patient are near the lower end of the scale (e.g., 7 mV*Hz or less), the portable treatment controller proceeds directly to state 885 and, subsequently, to state 890, as the application of defibrillation may be the patient's best chance for survival. As noted previously, in state 885, the portable treatment controller monitors transform values determined over smaller windows of time to predict when to apply defibrillation, adjusts the defibrillation parameters, and then, in state 890, applies the defibrillation at a time when the patient's transform values are trending toward a local maximum value.

In response to determining in state 855 that the patient's transform values are intermediate (between approximately 10 mV*Hz and 20 mV*Hz), but not indicative of a high probability of success, the portable treatment controller proceeds to state 870. In state 870, the portable treatment controller continues to monitor the ECG signals obtained from the body of the patient and determines updated transform values indicative of the metabolic state of patient's heart. The portable treatment controller also issues instructions, such as by a textual message on a visual display screen of the portable treatment controller or an associated watch, and audible instructions to any proximate bystanders, to perform CPR on the patient in an effort to improve the metabolic state of the patient's heart where defibrillation is more likely to be effective. After issuing the instructions to perform CPR on the patient, the portable treatment controller proceeds to state 880.

In state 880, the portable treatment controller continues to monitor the ECG signals obtained from the body of the patient and determines updated transform values indicative of the metabolic state of patient's heart. The portable treatment controller also monitors signals, such as those provided by the one or more accelerometers provided on the wearable treatment device, to determine whether CPR is being administered to the patient. In the event that the portable treatment controller determines that CPR is being administered to the patient, the portable treatment controller may continue to monitor the ECG signals and continue to determine transform values to detect whether the administration of CPR is having a beneficial effect. In the event that the CPR is having a beneficial effect, the portable treatment controller may continue to monitor the ECG signals and determine updated transform values until the probability of successful defibrillation (as indicated by the updated transform values) increases to a point where defibrillation is likely to be successful. In response to determining that defibrillation has a sufficiently high probability of success, the portable treatment controller may instruct the bystander to discontinue CPR and move away from the patient, so that the impedance reducing gel may be deployed in state 875, defibrillation parameters are determined based on transform in state 885, and a defibrillation shock is administered as described previously with respect to state 890. Alternatively, in response to determining by the portable treatment controller that CPR is not being administered to the patient, the portable treatment controller may proceed immediately to states 875, 885, and 890.

In some implementations, other metrics associated with the metabolic state of a patient's heart can also be used in various defibrillators, including defibrillators that are not non-invasive, ambulatory, and bodily attached, such as an Automated External Defibrillator (AED) or an Advanced Life Support (ALS) type of defibrillator. Transform values obtained over varying windows of time can be used to vary the type of therapy, and the timing of that therapy in such defibrillators. For example, transform values determined over successive smaller windows of time of about one second can be used in making a determination about timing and type of therapy in various commercially available defibrillators, including, for example, the M Series defibrillators, R Series ALS defibrillators, R Series Plus defibrillators, or E Series defibrillators manufactured by ZOLL Medical Corporation of Chelmsford Mass. In such defibrillators, defibrillation can be applied to the patient, for example, at a time when transform values are trending toward a local maximum to increase the probability of successful defibrillation.

Figure 9:
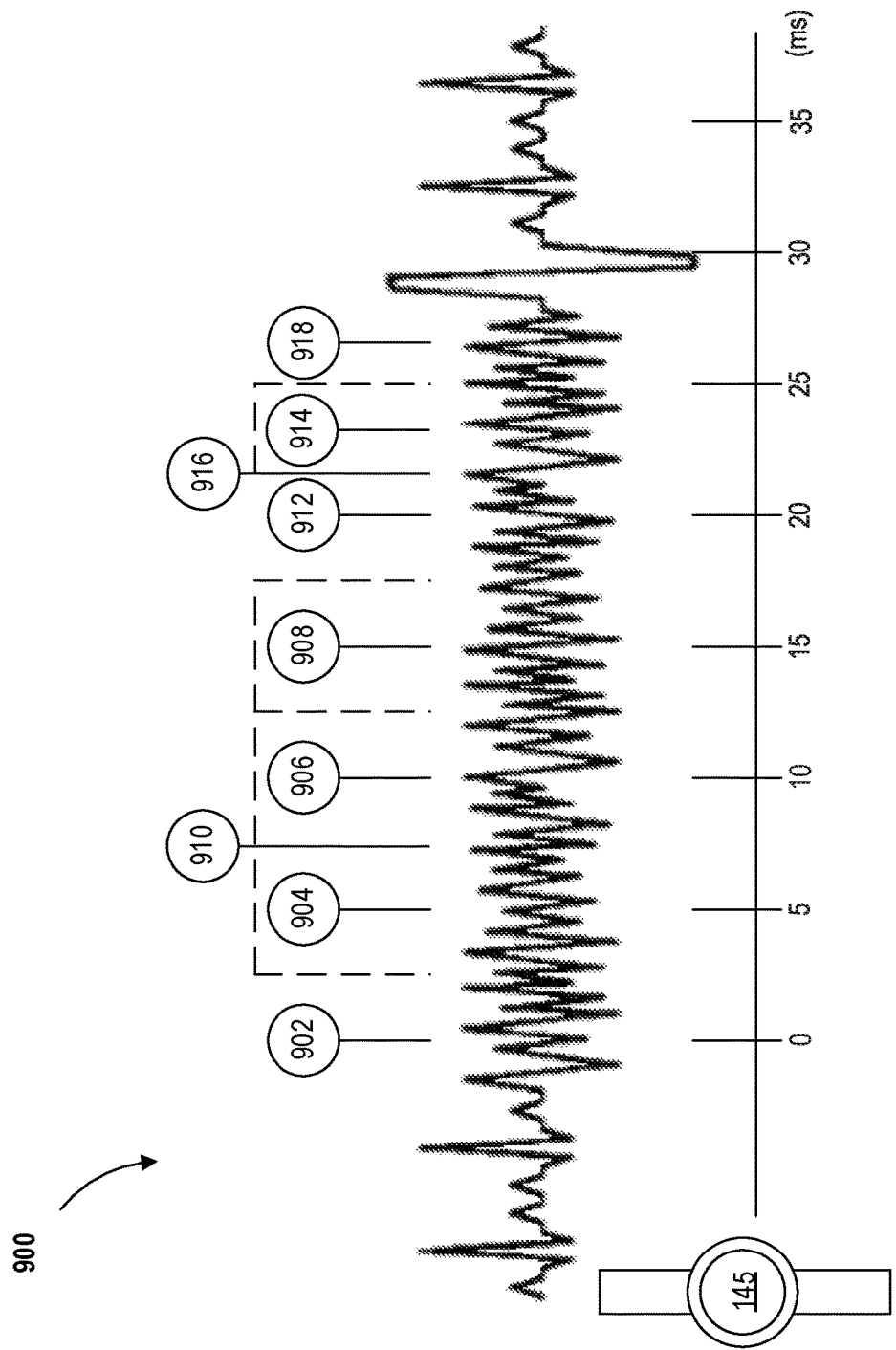
FIG. 9 is a diagram showing an example treatment alarm sequence, a timeline of operation of a non-invasive, bodily attached ambulatory medical monitoring and treatment device.

FIG. 9 illustrates a treatment alarm sequence, a timeline of operations from onset of an arrhythmia to delivery of an electrical shock treatment. The length of the sequence 900 is shown to be around 30 seconds. However, the length of the sequence 900 can be longer or shorter depending on certain factors. For example, if the potential arrhythmia rhythm is deemed to be a VT rhythm, a default response time for the patient may be 60 seconds, which can be adjusted to be in a range of 60 to 180 seconds. For example, if the potential arrhythmia rhythm is deemed to be a VF rhythm, a default response time may be 25 seconds, which can be adjusted to be in a range of 25 to 60 seconds. Thus, the duration of the sequence 900 can be adjusted to accommodate for these response times. If a treatment alarm sequence is ongoing, in some examples, based on the transform score and other inputs the device can hasten the application of the defibrillation shock so that the shock is delivered sooner than the default of configured time. Otherwise, the device can delay the shock, for example, an additional 25-45 seconds. At step 902, an arrhythmia is detected by an arrhythmia detection algorithm by a device or system, as described with reference to FIGS. 1, 2, and 5. The arrhythmia detection algorithm includes multiple techniques for digitally processing a plurality of physiological signals (e.g., ECG) to generate an arrhythmic score and to extract information associated to a potential onset of arrhythmia in real-time. The arrhythmia detection algorithm can be designed to continuously monitor ECG signals recorded and processed by a medical monitoring and treatment device (e.g., medical monitoring and treatment device 100 described with reference to FIG. 1A).

The arrhythmia detection algorithm includes a variety of features to identify and remove interference, reduce noise, and evaluate the quality of the signals. The arrhythmia detection algorithm uses a combination of heart rate analysis and/or morphology analysis to determine a treatable arrhythmia. For example, the arrhythmia detection algorithm can use heart rate, stability, morphology, and onset criteria to provide an accurate detection of arrhythmia. The morphology analysis is performed by comparing a baseline template vectorcardiogram to the patient's current vectorcardiogram. The morphology analysis provides a high degree of sensitivity and specificity in detection of arrhythmias, such as ventricular tachyarrhythmia.

The arrhythmia detection algorithm is designed to evaluate several rate inputs simultaneously to determine the patient's heart rate. For example, the arrhythmia detection algorithm can use two QRS detectors, one on each lead, to provide independent assessments of the heart rate, as described with reference to FIG. 5. ECG signal frequencies can be analyzed using a fast Fourier transform (FFT) algorithm, which decomposes an analog waveform into its frequency components and enables input signal analysis in the frequency domain. The FFT algorithm output is analyzed to determine the strongest frequency component indicative of heart rate. The FFT analysis can indicate the heart rate during ventricular tachycardia (VT) or ventricular fibrillation (VF). The morphology analysis algorithm is also used to determine the heart rate.

The arrhythmia detection algorithm applies logical weights based on comparing leads, signal quality, and historic rate values in order to determine the best inputs to accurately monitor the patient's heart rate. For example, if the heart rate from two QRS detectors does not match, the corresponding weight is decreased and the weight corresponding to other sources can be maintained constant or increased.

The arrhythmia detection algorithm uses the adjusted weights to determine the arrhythmic score. For example, any of the following appropriate steps may be taken: an arrhythmic score may be generated for each of the leads, the leads scores may normalized (e.g., to a 0 to 1 or 0 to 300 scale), a weighting may be applied to each of the scores to represent a determined reliability of the respective lead, the arrhythmic scores may be totaled or otherwise combined, and an indication of treatment necessity can be determined such as a go/no go indication. The indication can be determined by comparing the arrhythmic score to one or more thresholds, such as a VT threshold and a VF threshold. The VT and VF thresholds are programmed for the patient during the setup of the device. If the rate exceeds the VT or the VF threshold, the algorithm then proceeds to a morphology analysis comparing the patient's normal rhythm baseline template, obtained during device setup, to the current QRS morphology.

The morphology analysis uses two leads in normal operation. These substantially orthogonal leads (front-to-back and side-to-side) are positioned circumferentially at the level of the xiphoid process. The vectorcardiogram formed from these signals is compared in real time with the patient's normal rhythm baseline template. Failure to match the real time vectorcardiogram and baseline morphology templates contributes to the device's determination that a treatable arrhythmia exists. If the current vectocardiogram and the baseline template match, the treatment algorithm continues to monitor the patient. If the signal quality from one of the leads is deemed unreliable, morphology analysis is not used. Instead, the algorithm relies primarily on the heart rate, stability, and onset criteria. The stability criteria are measured by monitoring R-to-R wave intervals. The onset criteria are determined by rapid changes in the heart rate.

The arrhythmia detection algorithm can determine a confidence level as part of the process for deciding to treat or not to treat an arrhythmia. The confidence level is the sum of the individually weighted input factors of heart rate, morphology, response button use, signal quality, and spectral analysis. The input factors can contribute positively or negatively to the confidence level. If an input factor is deemed unreliable, its weight can be lessened or redistributed entirely to other factors.

Once an arrhythmia is determined, the treatment confidence algorithm decides if the rhythm is treatable based on the duration or persistence of the arrhythmia and identification of the arrhythmia as a VT/VF event. If the confidence level falls below a specified level, the treatment sequence is terminated and the system reverts to monitoring for a new arrhythmia.

The arrhythmia detection algorithm can generate a decision regarding a treatable arrhythmia approximately five to six seconds from the onset of the arrhythmia. The arrhythmia detection algorithm continues to monitor and reevaluates the decision regarding a treatable arrhythmia for approximately ten additional seconds before a treatment alarm sequence requesting a response from the patient begin. The arrhythmia confirmation time reduces the incidence of false arrhythmia alarms.

At step 904, the treatment alarm sequence requesting a response from the patient is initiated to verify that the patient is unconscious. For example, the treatment alert sequence includes an alert is initiated and maintained at a first level for about 5 seconds. For instance, an initial alert may be a vibration alert delivered to the patient. In this manner, in response to determining and confirming the existence of an arrhythmia, in particular, a ventricular fibrillation rhythm, it is determined if the patient is conscious through a treatment alarm sequence of a series of vibration, voice, and siren alerts. If the patient does not respond by pressing and holding the response buttons after a preset amount of time (e.g., 25 seconds for a VF event), the device automatically proceeds to treating the patient. The patient interaction feature provides the unique advantage of potentially eliminating inappropriate treatments, such as when the patient is conscious. For example, if a patient uses the response buttons after hearing the alarms and the heart rate slows, the confidence level decreases. If the patient releases the response buttons or does not interact with any of the response buttons and the heart rate increases or becomes abnormal, the treatment confidence increases as the patient may have lost consciousness. The patient responsiveness test begins discretely with a silent vibration and illumination of the response buttons, providing the patient the opportunity to respond without disrupting a social environment. The expected consciousness response is for the patient to activate (e.g., hold) the response buttons on the monitor. If the patient properly responds to the alarm to confirm consciousness, the treatment alarm sequence can be delayed for a preset duration, e.g., between 25 to 45 seconds. After this duration ends, if the arrhythmia continues to persist, the device can re-initiate the treatment alarm sequence.

At step 906, the treatment alarm sequence continues with an alert that is escalated to a second level and maintained at the second level for about 5 seconds. The second level of the alert can include a low-volume dual-tone siren. The siren can get louder (e.g., to about 100 decibels) to reach a volume that could awaken a potentially sleeping patient.

At step 908, the treatment alarm sequence may escalate to a first audible prompt that is issued and repeated for about 5 seconds. The first audible prompt indicates that an electrical shock is possible. For example, if the patient is not responsive, the first audible prompt can include voice messages that warn bystanders of a possible treatment shock. The voice messages can be interspersed with the high-volume siren.

At step 910, first transform value (e.g., an AMSA value) is for the VT/VF signal determined and used to identify an energy level of an electric shock, expected to successfully restore the cardiac rhythm of the patient (as described with reference to FIG. 3). In some implementations, the first transform value is determined in response to the alert being initiated. In some implementations, the first transform value is determined in response to the alert being escalated. In some implementations, the first transform value is determined in response to issuing the first audible prompt.

At step 912 gel is released to the patient chest in preparation of the electric shock delivery. At 914, a second audible prompt is issued. The second audible prompt indicates a bystander not to touch or cease contact with the patient. In some implementations, the second audible prompt is repeated multiple times within an interval of about 3 to 5 seconds.

At optional step 916, a second transform value (e.g., a second AMSA value) is determined for the VT/VF event. In some implementations, the second transform value is determined in response to the gel being released. In some implementations, the second transform value is determined in response to the second audible prompt being issued. In some implementations, the second transform value may be determined substantially duration or at the same time as step 912 when the gel is released in preparation of the shock delivery. The second transform value is compared to the first transform value and an energy level of the electric treatment is adjusted based on the comparison (as described with reference to FIG. 3).

At step 918, the treatment shock having the energy level determined based on one or more of the first and second transform values (e.g., a magnitude of difference between the first and second transform values) is delivered to the patient. In the example sequence 900 of FIG. 9, the treatment shock is delivered approximately 27 seconds after the onset of the cardiac arrhythmia.

Figure 10:
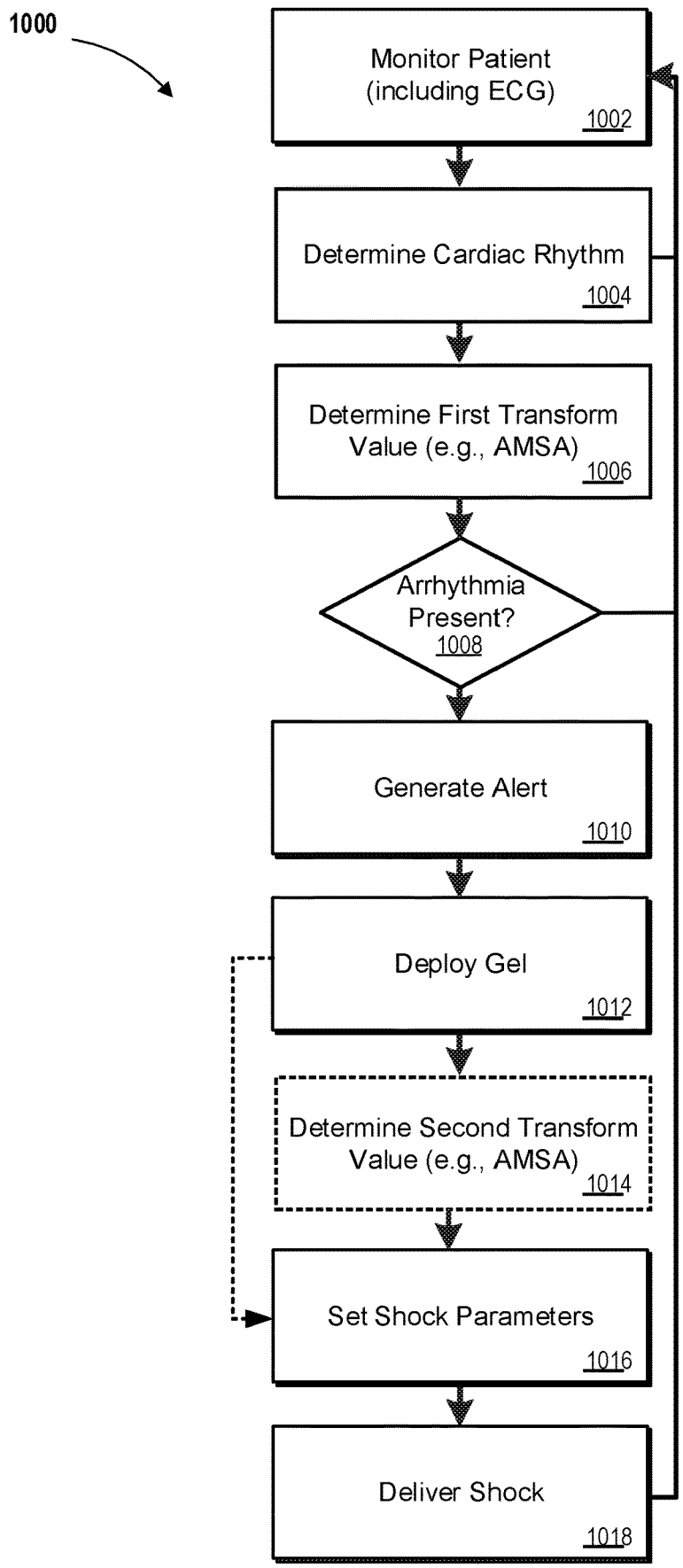
FIG. 10 is a flowchart of a process performed by a non-invasive, bodily attached ambulatory medical monitoring and treatment device.

FIG. 10 is a flow chart of a process 1000 for determining an energy level for a treatment shock to be delivered by a medical monitoring and treatment device (e.g., medical monitoring and treatment device 100 described with reference to FIG. 1A). In general, the process 1000 involves collecting data from a patient who is being automatically treated by the device and using that data to identify an appropriate energy level to deliver in a future shock to the patient, if it is determined that the patient is in need of and susceptible to a defibrillating shock. In particular, the data may include ECG data collected from electrodes placed on the patient, and processed using an arrhythmia detection algorithm implemented in the device.

The process 1000 begins at 1002, where a patient is generally monitored by the medical device, such as a LifeVest® Wearable Cardioverter Defibrillator available from ZOLL Medical Corporation of Chelmsford, Mass. The monitoring may occur substantially continuously, in a typical manner, and data from the monitoring may be displayed on the medical device, such as by displaying a continuous readout of the patient's pulse, ECG, blood pressure, and other relevant medical information.

At step 1004, a cardiac rhythm of the patient is determined. For example, the cardiac rhythm may be a normal cardiac rhythm of the patient such as a normal sinus rhythm, or other non-shockable cardiac arrhythmia rhythms that is not treated by defibrillation therapy, such as certain VT rhythms, a tachycardia rhythm or a bradycardia rhythm. Using a VT/VF detection algorithm, process 1000 may classify the cardiac rhythm of the patient as a shockable VT or shockable VF arrhythmia rhythm (see step 1008).

At step 1006, a first transform value of the cardiac rhythm is determined as described herein. In some implementations, the first transform value is calculated based on the determined cardiac rhythm whether or not the cardiac rhythm is a VT or VF arrhythmia event. In such implementations, a determination of whether the cardiac rhythm is classified as a VT or VF event may occur later in the process (e.g., in step 1008). In this regard, the first transform value may be calculated in a similar manner as described with reference to FIG. 1B, for example, as an AMSA transform value. Accordingly, the first transform value may be determined from the ECG signals corresponding to the cardiac rhythm of the patient, for example, by applying a fast Fourier transfer (FFT) to multiple dimensions of the ECG data as described above. The frequency transformations may occur via the use of vectorized FFTs applied to vectors formed by different (two or more) leads that have collected the ECG data.

As noted, the first transform value can be used to classify the cardiac rhythm as, for example, a normal sinus rhythm, a shockable VT or VF rhythm and, a noisy rhythm. While the first transform value may be used as is in such a classification process, in some implementations, the first transform value may be normalized to a different scale. For instance, the first transform value may be represented by a binary score, where 0 indicates a potential false arrhythmia event, such as a noise rhythm, and 1 indicates a VT/VF event. The binary score can be determined based on a comparison of, e.g., 3-5 second ECG segment values to a threshold. Such thresholds may be user-configurable and preset in the device prior to monitoring.

As the transform value is generally a sum of weighted spectral components around 40 Hz, these components typically lie outside the physiologic bandwidth of 3-15 Hz, and as such transform values such as AMSA values tends to be sensitive to high frequency ECG noise. For example, an AMSA values in excess of a predetermined threshold of around 30 mV*Hz may be considered to be indicative of a noise rhythm. Accordingly, if the first transform value is greater than around 30, a second arrhythmia score may indicate that the potential arrhythmia rhythm is noise a noise rhythm. Alternatively, if the AMSA value is less than around 30, the second arrhythmia score may indicate that the potential arrhythmia rhythm is a VT or VF rhythm.

In some examples, a ratio between an AMSA value and a time domain peak-peak or root mean square amplitude (RMS) amplitude may also be indicative of a high frequency noise in the signal. Accordingly, the processor (e.g., processor 218 of FIG. 2) may be configured to compute such a ratio in real time. For example, a combination of lower time domain amplitudes and higher AMSA values may be a strong indicator of high frequency noise. Accordingly, a ratio of AMSA/RMS amplitude of the ECG signal may be used to determine whether a potential arrhythmia rhythm is a VT or VF rhythm or a noise rhythm. In implementations, the RMS amplitude is unitless and can be normalized to 1 (e.g. an RMS amplitude of 500 microvolts would have value of 0.5). In such implementations, an example predetermined threshold for noise detection may be set to 45.

At step 1008, the cardiac rhythm determined in step 1004 can be analyzed by a VT/VF arrhythmia algorithm (see, e.g., FIG. 9 and associated description) to determine whether the cardiac rhythm is a VT/VF rhythm. If the cardiac rhythm is deemed to be a VT/VF event, then the first transform value may be used as a measure of a likelihood of shock success and/or to set one or more energy delivery parameters as described herein. In certain implementations, the first transform value may be calculated after determining the presence of a VT/VF rhythm (e.g., after step 1008).

The power spectrum area can be measured and its value can be used as an input that is alternative to, or in addition to, the first transform value for likelihood of shock success and/or to set one or more energy delivery parameters. Rather than treating each shock as a discrete event in analyzing the probability of success, the techniques described here can take into account prior shock deliveries, and an observed response of the patient to those deliveries, in determining an transform value or other value that indicate that a shock currently applied to the patient will likely be successful (or not) in defibrillating the patient (as described with reference to FIG. 3). Such a determination may also be combined with determinations about trans-thoracic impedance (trans-thoracic impedance) of the patient, or other measured factors, as discussed more fully below.

To obtain better predictive value for the first transform values, the time window, from which the ECG data for a transform determination is taken may be made relatively small (e.g., between 3 and 4 seconds, between 2 and 3 seconds, and between 1 and 2 seconds), which places the data as close to the current status of the patient as possible. Smaller windows may suffer from edge effects more-so than would larger windows, so the shape (e.g., a tapered window) and coefficients for the windows may also be selected to maximize predictive power of the method. For example, a Tukey window having appropriate coefficients may be employed, and the measurements may be made across multiple scalar lead values with the data being processed as a vector representation of those scalar values.

The techniques discussed with reference to process 1000 receive input from a plurality of ECG leads based on electrodes disposed within a garment worn about the torso of the patient and characterize that input as a vector value, where the vector that may be made up of three orthogonal (X, Y, and Z) vectors from the plurality of leads and can be understood as rotating through a complex space with each cycle of a heartbeat. A complex FFT operation may be conducted on the vector representation in order to compute the first vectorized amplitude spectrum area (AMSA) transform value, where the first AMSA transform value is a numerical value that is based on the sum of the magnitude of a weighted frequency distribution from the signal, e.g., between 3 and 48 Hz. Generally, the greater the AMSA, the greater the probability that an applied shock defibrillates the heart successfully (as described with reference to FIG. 3).

The particular parameters for computing the vectorized AMSA value may be selected so as to maximize the predictive capabilities of a medical device. For example, a tapering function may be applied to the ECG data window (e.g., by using a Tukey window), so as to improve the accuracy of the FFT applied to the data. Such a tapered window may prevent the data from jumping immediately from a zero value up the measured values, and then back down immediately to a zero value at the end of a measured window. Various parameters for the tapering function may also be applied, such as coefficients to define the slopes of the starting and ending edges of the function. Moreover, the length of the window may be selected to provide better data, such as by using a relatively short window having a duration shorter than 4 seconds, and in some examples of about 1 second, between 1 and 2 seconds, between 1 and 3 seconds, between 2 and 3 seconds, or between 3 and 4 seconds long.

In certain other implementations, multiple different tapering functions may be applied to the same data essentially simultaneously, transform values may be determined from each such applied function, and the resulting first transform value from one of the functions may be selected, or the first transform value may be generated that is a composite from multiple different tapering functions. The window function that is used, the length of the window, and the coefficients for the window may also be adjusted dynamically, so that one or more of them change during a particular incident, or deployment, with a particular patient. For example, it may be determined from analysis of prior data that a certain window shape, size, and/or coefficients are better earlier in an episode of VF than later, so that a defibrillator may be programmed to change such parameters over the course of an event.

Such changes may be tied to an initial determination about how long the patient has been in VF, as estimated by the device. Also, changes to the window type, size, and coefficients may be made from readings dynamically made from the patient under treatment. For example, first transform values in a particular range may be measured better by a particular window type, size, or range of coefficients, so that the first AMSA measurement made at time n that shows such a value, may be measured using the other parameters known to work best with that transform value at time n+1. Other techniques for dynamically adjusting the window type, window size, and/or coefficients may also be employed.

At step 1010, in response to determining that a VT/VF event is ongoing, an alert is generated based on the confirmation of the VT/VF rhythm. The alert can be a sound alert, a haptic alert, a visual alert, or a combination of alert types. In some implementations, shock indications are provided to the rescuer. Such indications may include the energy level that has been computed by the device as well as an indication of a likelihood of a shock that is currently delivered being a success in defibrillating the patient. Such presentation, as indicated above and below, may include displaying a percentage likelihood of the shock succeeding, displaying a letter grade, or displaying a binary indication that a shock is or is not currently advised. The presentation may also be audible or haptic. Additional information provided to a rescuer may take the form of instructions, such as instructions to perform chest compressions or some other action, where the action is selected from among a plurality of possible treatments based on the current phase for the victim. A system may also integrate both automatic and manual approaches—e.g., locking out the ability to provide a shock until a threshold level is reached, and then showing the relative likelihood of success above that value. The likelihood of success can be shown in various manners, such as by showing an actual percentage, or showing two or more of a low, medium, or high likelihood of success, e.g., on an electronic display of a defibrillator.

At step 1012, gel is deployed to prepare the treatment area for delivery of the electric shock. In some implementations, at 1014, a second transform value (e.g., also an AMSA value) may be determined using the same or a similar computation protocol as used at step 1006. In some implementations, step 1014 may be optional and the processor 1000 may proceed to set shock parameters (step 1016) based on the first transform value AMSA calculated in step 1006. The second transform value is compared to the first transform value to identify more generalized changes in the patient's transform values, rather than using a single transform value corresponding to an isolated point in time. For example, the first and second transform values can be computed for particular points in time or particular windows in time and those values can be saved (e.g., in memory of the medical device). After multiple such measurements and computations have been made, an average may be computed across multiple such values. Because AMSA generally falls (on average) over time in an episode, if the average for a certain number of readings (e.g., a moving average) falls below a particular value or falls below the value over a minimum time period (so as to indicate the general AMSA condition of the victim rather than just a transient reading), the device may provide additional feedback or perform alternative operations.

Given that the patient is continuously monitored and the arrhythmia is detected within seconds after the onset, it is expected that the patient is in the electrical phase (the first several minutes of an event) that marks a period, during which an electric shock can be particularly effective in defibrillating the victim's heart and returning the victim to a relative satisfactory condition. In some implementations, AMSA can be compared to one or more thresholds to confirm if the patient is the electrical phase or in circulatory or metabolic phase. The circulatory phase appears to mark a decrease in effectiveness for electric shock in defibrillating the victim, and particularly in the absence of chest compressions performed on the victim. As a result, a device such as a wearable defibrillator may be programmed to stop advising shocks during such a phase (or may advise a shock only when other determinations indicate that a shock would be particularly likely to be effective) and may instead advise forceful CPR chest compressions. Such forceful compressions may maximize blood flow through the heart tissue and other parts of the body so as to extend the time that the victim may survive without lasting or substantial damage. In the metabolic phase, chest compressions may be relatively ineffective as compared to the circulatory phase. For example, where tissue has become ischemic, such as in circulatory phase, the tissue may react favorably to the circulation of blood containing some oxygen, but where tissue has become severely ischemic, such as in the metabolic phase, the introduction of too much oxygen may be harmful to the tissue. As a result, more gentle compressions for the first period, such as 30 seconds, may need to be advised in the metabolic phase before the rescuer (or a mechanical chest compressor controlled to provide appropriate levels of compression following the points addressed here) uses a full force. In some implementations, process 1000 continues from step 1012 directly to step 1016.

At step 1016, the therapeutic and/or shock delivery parameters are selected or adjusted based on determined transform values (e.g., first transform value, the second transform value or a combination of first and second transform value) and additional parameters indicating the state of the patient. The additional parameters can include cardiac-related information (e.g., electrocardiogram (ECG) information, including arrhythmia information, heart vibrations, etc.) and/or non-cardiac information (e.g., blood oxygen, the patient's temperature, glucose levels, tissue fluid levels, and/or lung vibrations).

Examples of such therapeutic and/or shock delivery parameters include, but are not limited to: peak defibrillation current or energy values, peak-to-peak defibrillation current or energy values first phase average defibrillation current or energy, defibrillation current or energy waveform duration, defibrillation peak voltage, defibrillation current or energy waveform rise or fall-time, defibrillation current or energy tilt values, defibrillation average current or energy values, and defibrillation RMS current or energy values. Other defibrillation current, voltage, and/or energy parameters may be modified based on the transform values described herein. Such determination may occur by applying a value from a shock prediction algorithm, such as an AMSA transform value, to a predefined formula, to a lookup table, or by way of other mechanisms for determining an energy level to supply. In some implementations, a ratio between the TTI value and the AMSA transform value may be used in a similar manner (e.g., by applying it to a formula, look-up table, etc.). The determination may also take into account other variables, either as part of combining those variables with the AMSA and TTI values, or by applying corrections after an initial determination is made using AMSA, TTI, or both.

At step 1018, the capacitor or multiple capacitors of the device may be charged to the determined energy level to deliver a shock. Such charging may occur automatically, or may occur at a later point in the process, such as after the patient has been irresponsive to one or more alerts within a given time period. The computed energy level and charging of capacitors may, in certain circumstances, occur only after the process has determined that the patient has a shockable cardiac arrhythmia rhythm, so that a shock is advised at all. The determination of a shockable cardiac arrhythmia rhythm may be part of determining a likelihood of success for applying a shock or may be separate from such a determination. For example, the determination of a shockable rhythm may be a threshold step before making further calculations and may be a relative simple determination to make. In contrast, the determination of a likelihood of success may be more complex and may occur after a shock of an old rhythm is determined.

In response to determining that the likelihood of treatment success is sufficient, the capacitor delivers the shock to the patient. In some implementations, the capacitor may be pre-charged to a level that does not match the level determined by the device when the shock is going to be provided. In such circumstances, additional charge may be provided to the capacitors or charge may be released from the capacitors before delivering the shock, so that the energy level that is determined or selected may be the appropriate energy level delivered to the patient. The medical device automatically delivers a shock at the time and with an energy level that is most appropriate and most likely to restore a cardiac rhythm of the patient. As a result, the patient may be given fewer shocks with less damage from potentially failed shocks.

Having thus described several aspects of at least one embodiment of the technology, it is to be appreciated various alterations, modifications, and improvements can readily occur to those skilled in the art. Such alterations, modifications, and improvements are intended to be part of the disclosure, and are intended to be within the scope of the following claims.

What is claimed is:

1. An ambulatory medical monitoring and treatment device comprising:
   a power source;
   a therapy delivery interface, coupled to the power source;
   a plurality of therapy electrodes coupled to the therapy delivery interface;
   a plurality of electrocardiogram (ECG) sensing electrodes to sense ECG signal of a heart of a patient;
   a sensor interface to receive and digitize the ECG signal; and
   at least one processor coupled to the sensor interface and the therapy delivery interface, the at least one processor configured to:
      analyze the ECG signal to determine a cardiac rhythm and a first transform value that represents a magnitude of at least one frequency component of the cardiac rhythm,
      analyze the cardiac rhythm and the first transform value to detect a shockable cardiac arrhythmia by
         classifying the cardiac rhythm as one of a noise rhythm and a shockable cardiac arrhythmia rhythm based at least in part on the first transform value, and
         causing the at least one processor to detect the cardiac arrhythmia in response to classifying the cardiac rhythm as a shockable cardiac arrhythmia rhythm,
      initiate a treatment alarm sequence requesting a response from the patient to verify that the patient is unconscious in response to detecting the shockable cardiac arrhythmia,
      initiate a release of a conductive gel on the patient's chest,
      determine a second transform value that represents a current magnitude of the at least one frequency component of the cardiac rhythm after the release of the conductive gel,
      adjust, based on the first and second transform value, at least one shock delivery parameter for a defibrillation shock, and
      cause the therapy delivery interface to provide the defibrillation shock via the plurality of therapy electrodes based on the at least one shock delivery parameter on receiving no response from the patient.

2. The device of claim 1, wherein the at least one processor is configured to initiate the treatment alarm sequence to generate an alert in response to detecting the shockable cardiac arrhythmia, the alert indicating detection of the shockable cardiac arrhythmia.

3. The device of claim 2, wherein the alert is a first alert and prior to initiating the release of the conductive gel, the at least one processor is configured to generate a second alert indicating shock delivery.

4. The device of claim 1, wherein the at least one processor is configured to perform a comparison between the first transform value and the second transform value and adjust the at least one shock delivery parameter based on the comparison.

5. The device of claim 4, wherein the first transform value and the second transform value are determined over a window of time of 100 milliseconds to twenty seconds.

6. The device of claim 4, wherein the first alert is generated over a window of time of about twenty seconds and the second alert is generated over a window of time of about fifteen seconds.

7. The device of claim 1, wherein the at least one shock delivery parameter is a peak current value.

8. The device of claim 1, wherein the at least one shock delivery parameter is defibrillation energy waveform duration.

9. The device of claim 1, wherein the at least one shock delivery parameter is at least one of a defibrillation current waveform rise time, a shock energy, and a defibrillation peak voltage.

10. The device of claim 1, wherein generating the transform value comprises applying one or more Fast Fourier Transforms (FFTs) to data representing the ECG signal.

11. The device of claim 10, wherein the FFTs comprise vectorized FFTs applied to vectors formed from data obtained by different leads for the ECG signal.

12. The device of claim 11, wherein generating the transform value comprises one or more amplitude spectrum area calculations applied to the data representing the ECG signal.

13. The device of claim 1, wherein generating the transform value comprises computing a mathematical transform from a time domain to a frequency domain on a window of the ECG signal.

14. The device of claim 1, wherein generating the transform value comprises summing products of a plurality of magnitudes of frequency components with a plurality of weighting factors within a predetermined spectrum.

15. The device of claim 14, wherein the plurality of weighting factors is in a nonlinear relationship with the frequency components within the predetermined spectrum.

16. The device of claim 14, wherein the plurality of weighting factors has a pre-established linear or nonlinear relationship with the magnitudes of the frequency components.

17. The device of claim 1, wherein the sensor interface receives an additional parameter indicative of a state of the patient, the additional parameter comprising a cardiac information or a non-cardiac information.

18. The device of claim 17, wherein the at least one processor is configured to adjust the at least one shock delivery parameter for the defibrillation shock based on the additional parameter.

19. An ambulatory medical monitoring and treatment device comprising:
   a power source;
   a therapy delivery interface, coupled to the power source;
   a plurality of therapy electrodes coupled to the therapy delivery interface;
   a plurality of electrocardiogram (ECG) sensing electrodes to sense ECG signal of a heart of a patient;
   a sensor interface to receive and digitize the ECG signal; and
   at least one processor coupled to the sensor interface and the therapy delivery interface, the at least one processor configured to:

analyze the ECG signal to detect a shockable cardiac arrhythmia rhythm, determine, from the ECG signal, a first transform value that represents a magnitude of at least one frequency component of the ECG signal, confirm, based at least in part on the first transform value, that the ECG signal comprises the shockable cardiac arrhythmia rhythm, initiate a treatment alarm sequence requesting a response from the patient to verify that the patient is unconscious, determine, from the ECG signal, a second transform value that represents another magnitude of another at least one frequency component of the shockable cardiac arrhythmia rhythm, adjust, based on the first transform value and the second transform value, at least one shock delivery parameter for a defibrillation shock, and cause the therapy delivery interface to provide the defibrillation shock via the plurality of therapy electrodes based on the at least one shock delivery parameter on receiving no response from the patient.

20. The device of claim 19, wherein the at least one processor is configured to initiate the treatment alarm sequence to generate an alert in response to detecting the shockable cardiac arrhythmia rhythm, the alert indicating detection of the shockable cardiac arrhythmia rhythm.

21. The device of claim 20, wherein the at least one processor is configured to initiate a release of a conductive gel on the patient's chest.

22. The device of claim 21, wherein the alert is a first alert and prior to initiating the release of the conductive gel, the at least one processor is configured to generate a second alert indicating shock delivery.

23. The device of claim 22, wherein the at least one processor is configured to perform a comparison between the first transform value and the second transform value and adjust the at least one shock delivery parameter based on the comparison.

24. The device of claim 22, wherein the first alert is generated over a window of time of about twenty seconds and the second alert is generated over a window of time of about fifteen seconds.

25. The device of claim 19, wherein the first transform value and the second transform value are determined over a window of time of 100 milliseconds to twenty seconds.

26. The device of claim 19, wherein the at least one shock delivery parameter is a peak current value.

27. The device of claim 19, wherein the at least one shock delivery parameter is at least one of a defibrillation current waveform duration, a defibrillation current waveform rise time, a shock energy, and a defibrillation peak voltage.

28. The device of claim 19, wherein generating each of the first transform value and the second transform value comprises applying one or more Fast Fourier Transforms (FFTs) to data representing the ECG signal.

29. The device of claim 28, wherein the FFTs comprise vectorized FFTs applied to vectors formed from data obtained by different leads for the ECG signal.

30. The device of claim 19, wherein generating each of the first transform value and the second transform value comprises computing a mathematical transform from a time domain to a frequency domain on a window of the ECG signal.

31. The device of claim 19, wherein generating each of the first transform value and the second transform value comprises summing products of a plurality of magnitudes of frequency components with a plurality of weighting factors within a predetermined spectrum, the plurality of weighting factors being in a nonlinear relationship with frequency components within the predetermined spectrum.

32. The device of claim 19, wherein the sensor interface receives an additional parameter indicative of a state of the patient, the additional parameter comprising a cardiac information or a non-cardiac information.

33. The device of claim 32, wherein the at least one processor is configured to adjust the at least one shock delivery parameter for the defibrillation shock based on the additional parameter.

34. A computer-implemented method for providing ambulatory medical monitoring and treatment to a patient, the method being executed using one or more processors and comprising:

receiving, by the one or more processors, an electrocardiogram (ECG) signal of a heart of a patient;

analyzing, by the one or more processors, the ECG signal to determine a cardiac rhythm applying one or more Fast Fourier Transforms (FFTs) to data representing the ECG signal to determine a transform value that represents a magnitude of the FFTs, the FFTs comprising vectorized FFTs applied to vectors formed from data obtained by different leads for the ECG signal;

analyzing, by the one or more processors, the cardiac rhythm and the transform value to detect a shockable cardiac arrhythmia by:

classifying the cardiac rhythm as one of a noise rhythm and a shockable cardiac arrhythmia rhythm based at least in part on the transform value, and causing the one or more processors to detect the cardiac arrhythmia in response to classifying the cardiac rhythm as a shockable cardiac arrhythmia rhythm;

initiating, by the one or more processors, a treatment alarm sequence requesting a response from the patient to verify that the patient is unconscious in response to detecting the shockable cardiac arrhythmia;

adjusting, by the one or more processors, based on the transform value, at least one shock delivery parameter for a defibrillation shock; and causing, by the one or more processors, a therapy delivery interface to provide the defibrillation shock via a plurality of therapy electrodes based on the at least one shock delivery parameter on receiving no response from the patient.

35. The computer-implemented method of claim 34, wherein generating the transform value comprises generating one or more amplitude spectrum area calculations applied to the data representing the ECG signal.

36. The computer-implemented method of claim 34, further comprising receiving an additional parameter indicative of a state of the patient, the additional parameter comprising a cardiac information or a non-cardiac information.

37. The computer-implemented method of claim 36, wherein selecting the at least one shock delivery parameter for the defibrillation shock is based on the additional parameter.

* * * * *

UNITED STATES PATENT AND TRADEMARK OFFICE
CERTIFICATE OF CORRECTION

PATENT NO. : 10,716,949 B2  
APPLICATION NO. : 15/924969  
DATED : July 21, 2020  
INVENTOR(S) : Gary A. Freeman et al.

It is certified that error appears in the above-identified patent and that said Letters Patent is hereby corrected as shown below:

In the Claims

Column 50, Line 9, Claim 6, delete "claim 4," and insert -- claim 3, --

Signed and Sealed this
Twenty-second Day of September, 2020

Andrei Iancu
*Director of the United States Patent and Trademark Office*